(12) United States Patent
Ryu et al.

(10) Patent No.: US 10,660,607 B2
(45) Date of Patent: May 26, 2020

(54) ULTRASOUND DIAGNOSIS APPARATUS FOR SELF-DIAGNOSIS AND REMOTE-DIAGNOSIS, AND METHOD OF OPERATING THE ULTRASOUND DIAGNOSIS APPARATUS

(71) Applicant: SAMSUNG ELECTRONICS CO., LTD., Suwon-si (KR)

(72) Inventors: Jae-young Ryu, Suwon-si (KR); Dong-ki Kim, Seoul (KR); Young-hwan Kim, Hwaseong-si (KR); Min-woo Seo, Seongnam-si (KR); Jei-young Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 516 days.

(21) Appl. No.: 15/500,398

(22) PCT Filed: Aug. 28, 2015

(86) PCT No.: PCT/KR2015/009098
§ 371 (c)(1),
(2) Date: Jan. 30, 2017

(87) PCT Pub. No.: WO2016/032298
PCT Pub. Date: Mar. 3, 2016

(65) Prior Publication Data
US 2017/0215842 A1 Aug. 3, 2017

(30) Foreign Application Priority Data
Aug. 28, 2014 (KR) .................. 10-2014-0113348

(51) Int. Cl.
*A61B 8/00* (2006.01)
*G06F 19/00* (2018.01)
(Continued)

(52) U.S. Cl.
CPC .............. *A61B 8/4245* (2013.01); *A61B 8/06* (2013.01); *A61B 8/085* (2013.01); *A61B 8/4263* (2013.01);
(Continued)

(58) Field of Classification Search
CPC .. A61B 8/06; A61B 8/08; A61B 8/085; A61B 8/0883; A61B 8/0891;
(Continued)

(56) References Cited

U.S. PATENT DOCUMENTS 6,705,992 B2   3/2004   Gatzke
7,806,824 B2  10/2010   Ohtake
(Continued)

FOREIGN PATENT DOCUMENTS

CN   1608592 A    4/2005
CN   101730505 A  6/2010
(Continued)

OTHER PUBLICATIONS

International Search Report and Written Opinion dated Dec. 15, 2015, issued by the International Searching Authority in counterpart International Application No. PCT/KR2015/009098 (PCT/ISA/220, 210, and 237).

(Continued)

*Primary Examiner* — Catherine M Voorhees
(74) *Attorney, Agent, or Firm* — Sughrue Mion, PLLC

(57) ABSTRACT

An ultrasound diagnosis apparatus and method enabling general users to easily acquire ultrasound images even when the users are unskilled at using ultrasound diagnosis apparatuses, and a non-transitory computer-readable storage medium having the ultrasound diagnosis method recorded thereon are provided. The ultrasound diagnosis apparatus includes a probe configured to acquire ultrasound data of an object; an image generation unit configured to generate an
(Continued)

ultrasound image of the object by using the ultrasound data; a probe location acquisition unit configured to acquire a location of the probe on the object; a display unit configured to display the location of the probe and a reference location on an image representing the object; and a control unit configured to determine whether the location of the probe corresponds to the reference location.

20 Claims, 21 Drawing Sheets

(51) Int. Cl.
*A61B 8/06* (2006.01)
*A61B 8/08* (2006.01)

(52) U.S. Cl.
CPC ............ *A61B 8/4427* (2013.01); *A61B 8/463* (2013.01); *A61B 8/465* (2013.01); *A61B 8/467* (2013.01); *A61B 8/468* (2013.01); *A61B 8/469* (2013.01); *A61B 8/488* (2013.01); *A61B 8/565* (2013.01); *G06F 19/321* (2013.01); *A61B 8/08* (2013.01); *A61B 8/0883* (2013.01); *A61B 8/0891* (2013.01); *A61B 8/587* (2013.01)

(58) Field of Classification Search
CPC ... A61B 8/4245; A61B 8/4263; A61B 8/4427; A61B 8/463; A61B 8/465; A61B 8/467; A61B 8/468; A61B 8/469; A61B 8/488; A61B 8/565; A61B 8/587; A61B 8/089
USPC ......................................................... 600/441
See application file for complete search history.

(56) References Cited

U.S. PATENT DOCUMENTS

| | | | |
|---|---|---|---|
| 9,005,127 B2 | 4/2015 | Azuma | |
| 9,451,930 B2 | 9/2016 | Abe | |
| 9,471,981 B2 | 10/2016 | Arai et al. | |
| 9,480,457 B2 | 11/2016 | Kondou | |
| 2004/0019270 A1* | 1/2004 | Takeuchi ................ | A61B 8/14 600/407 |
| 2005/0119569 A1* | 6/2005 | Ohtake ................... | A61B 8/00 600/437 |
| 2008/0146277 A1 | 6/2008 | Anglin et al. | |
| 2008/0262356 A1 | 10/2008 | Chalana et al. | |
| 2010/0174192 A1 | 7/2010 | Azuma | |
| 2012/0203107 A1 | 8/2012 | Kim | |
| 2012/0220876 A1 | 8/2012 | Hwang | |
| 2014/0018661 A1 | 1/2014 | Tsujita et al. | |
| 2015/0257735 A1* | 9/2015 | Ball ...................... | A61B 8/5261 600/440 |

FOREIGN PATENT DOCUMENTS

| | | |
|---|---|---|
| CN | 102626324 A | 8/2012 |
| CN | 103781426 A | 5/2014 |
| JP | 2002263101 A | 9/2002 |
| JP | 2006505294 A | 2/2006 |
| JP | 2009207800 A | 9/2009 |
| JP | 2010-201049 A | 9/2010 |
| JP | 2010233921 A | 10/2010 |
| JP | 2012-91042 A | 5/2012 |
| JP | 2012-147858 A | 8/2012 |
| JP | 5027922 B2 | 9/2012 |
| JP | 5410629 B1 | 2/2014 |
| JP | 2016-501605 A | 1/2016 |
| KR | 1020100057341 A | 5/2010 |
| WO | 2008/149573 A1 | 12/2008 |
| WO | 2012/124341 A1 | 9/2012 |
| WO | 2014/097090 A1 | 6/2014 |

OTHER PUBLICATIONS

Communication dated Nov. 27, 2015, issued by the Korean Intellectual Property Office in counterpart Korean Application No. 10-2014-0113348.
Communication dated May 31, 2016, issued by the Korean Intellectual Property Office in counterpart Korean Application No. 10-2014-0113348.
Communication dated Dec. 16, 2016, issued by the Korean Intellectual Property Office in counterpart Korean Application No. 10-2014-0113348.
Communication dated Apr. 9, 2018 issued by the European Patent Office in counterpart European Patent Application No. 15835199.9.
Office Action dated May 7, 2019 by the Japanese Patent Office in counterpart Japanese Patent Application No. 2017-502779.
Office Action dated Jul. 2, 2019 by the State Intellectual Property Office of P.R. China in counterpart Chinese Patent Application No. 201580045417.2.
Office Action dated Apr. 2, 2020 issued by Chinese Patent Office in counterpart Chinese Patent Application No. 201580045417.2.

\* cited by examiner

[Fig. 1]
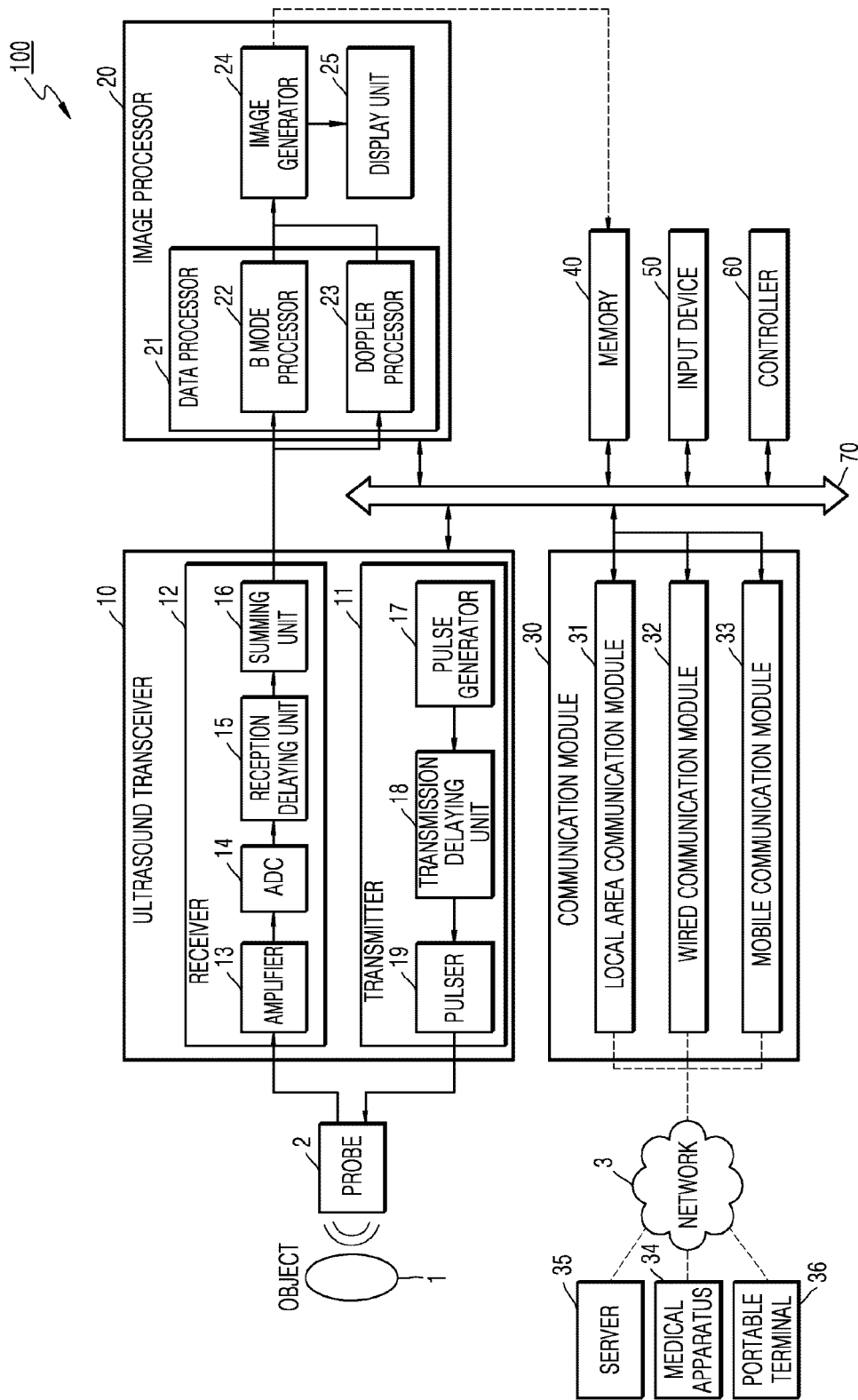

[Fig. 2]
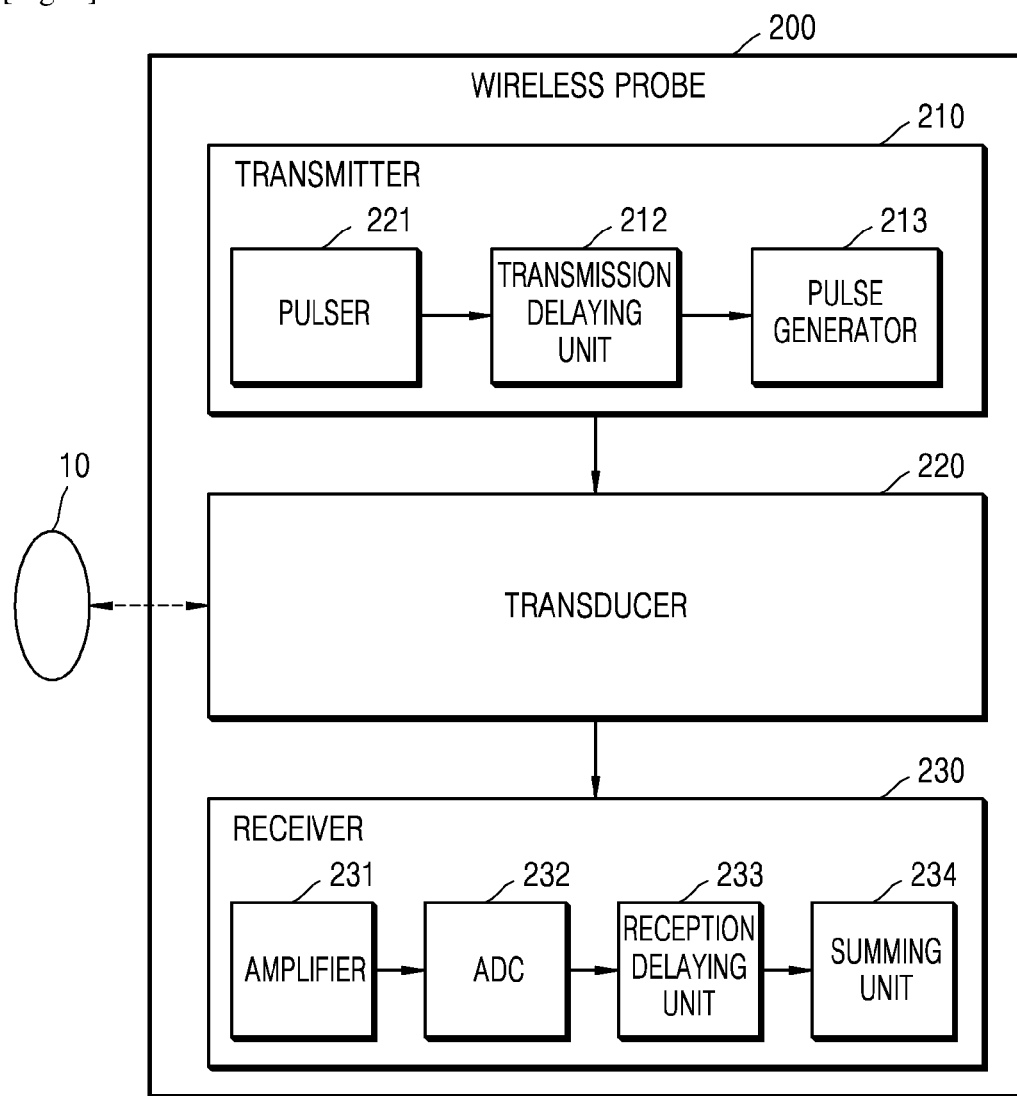

[Fig. 3]
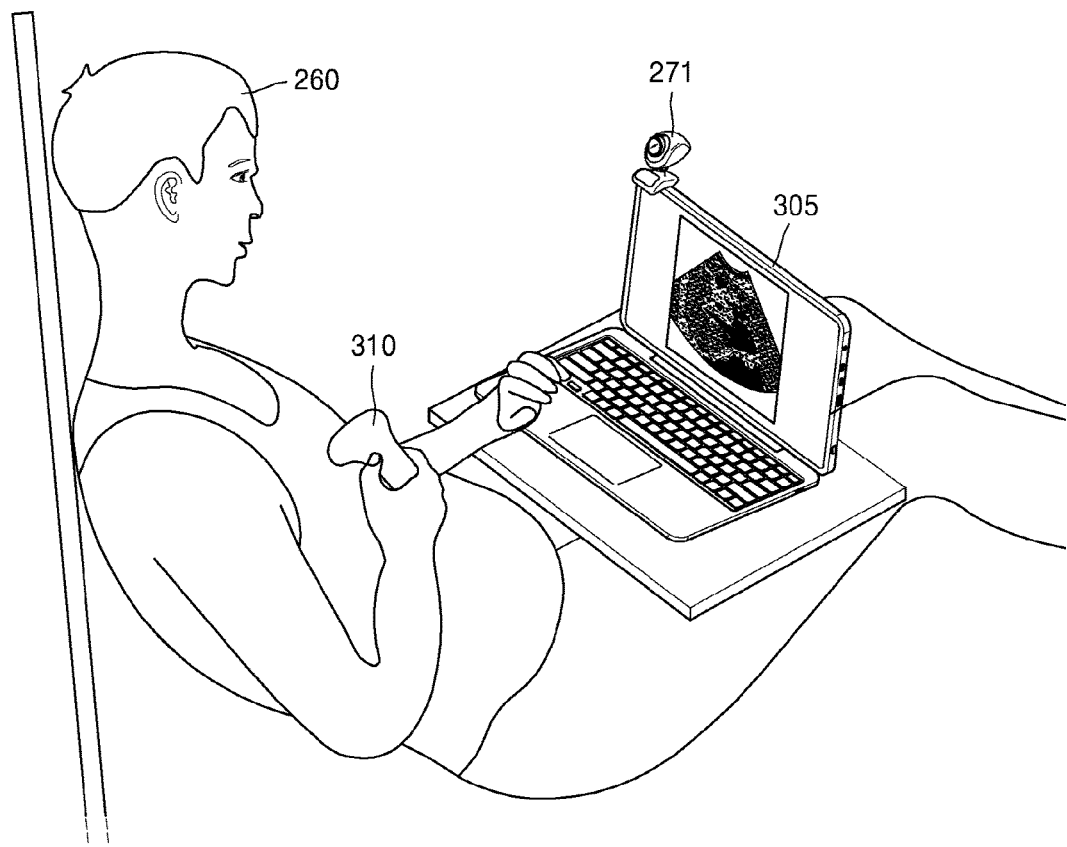
[Fig. 4]
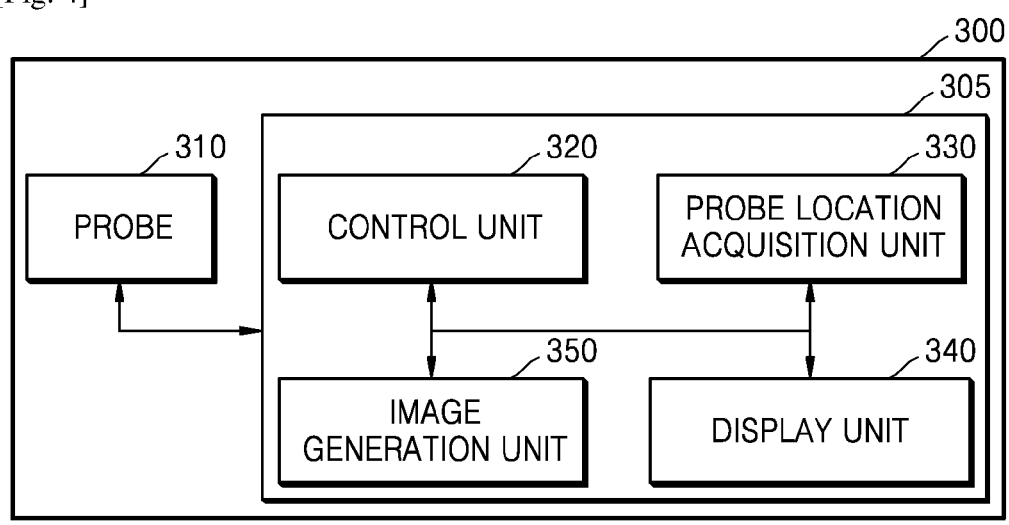

[Fig. 5]
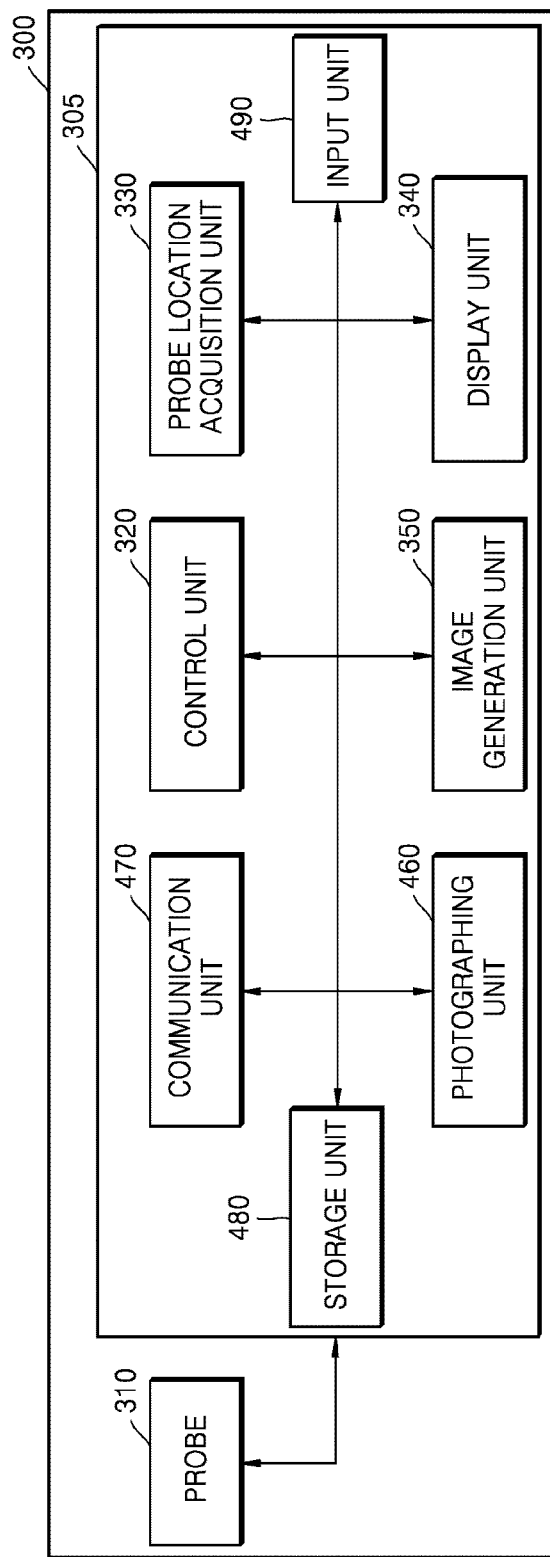

[Fig. 6A]
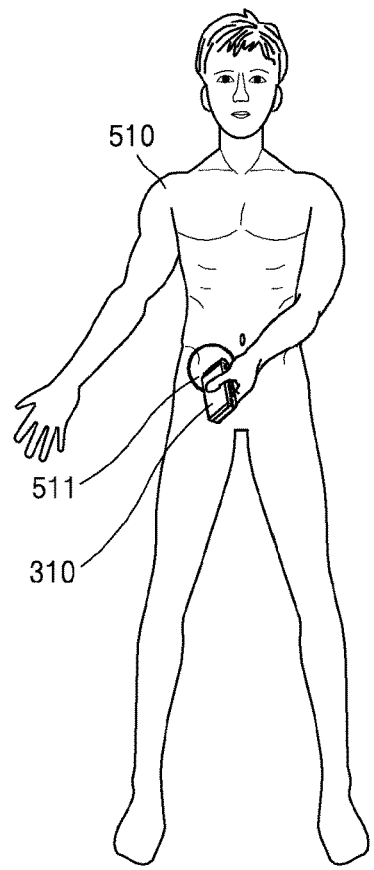
[Fig. 6B]
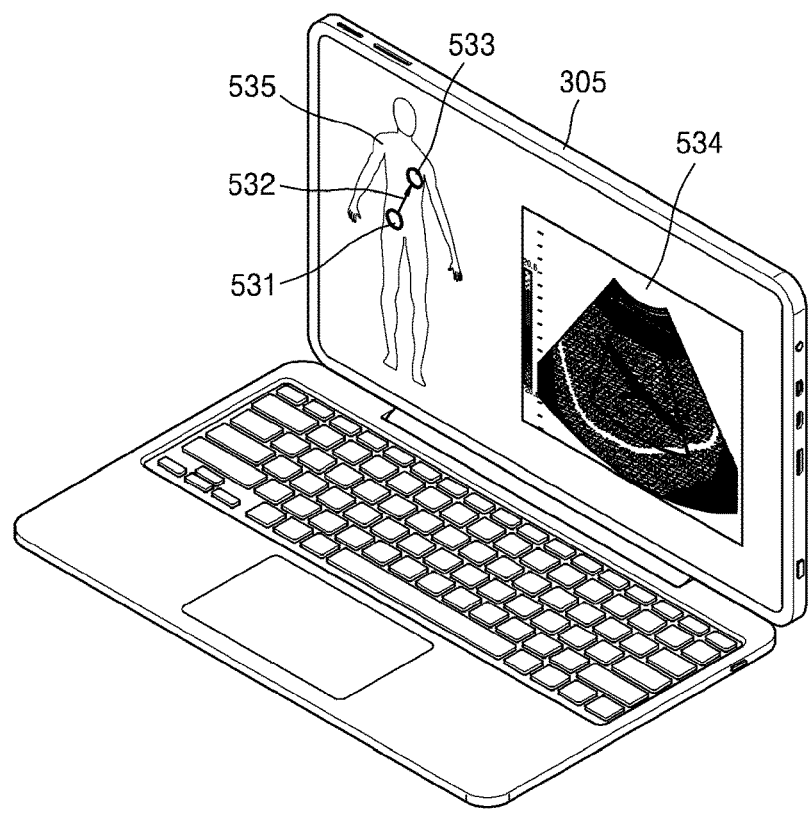

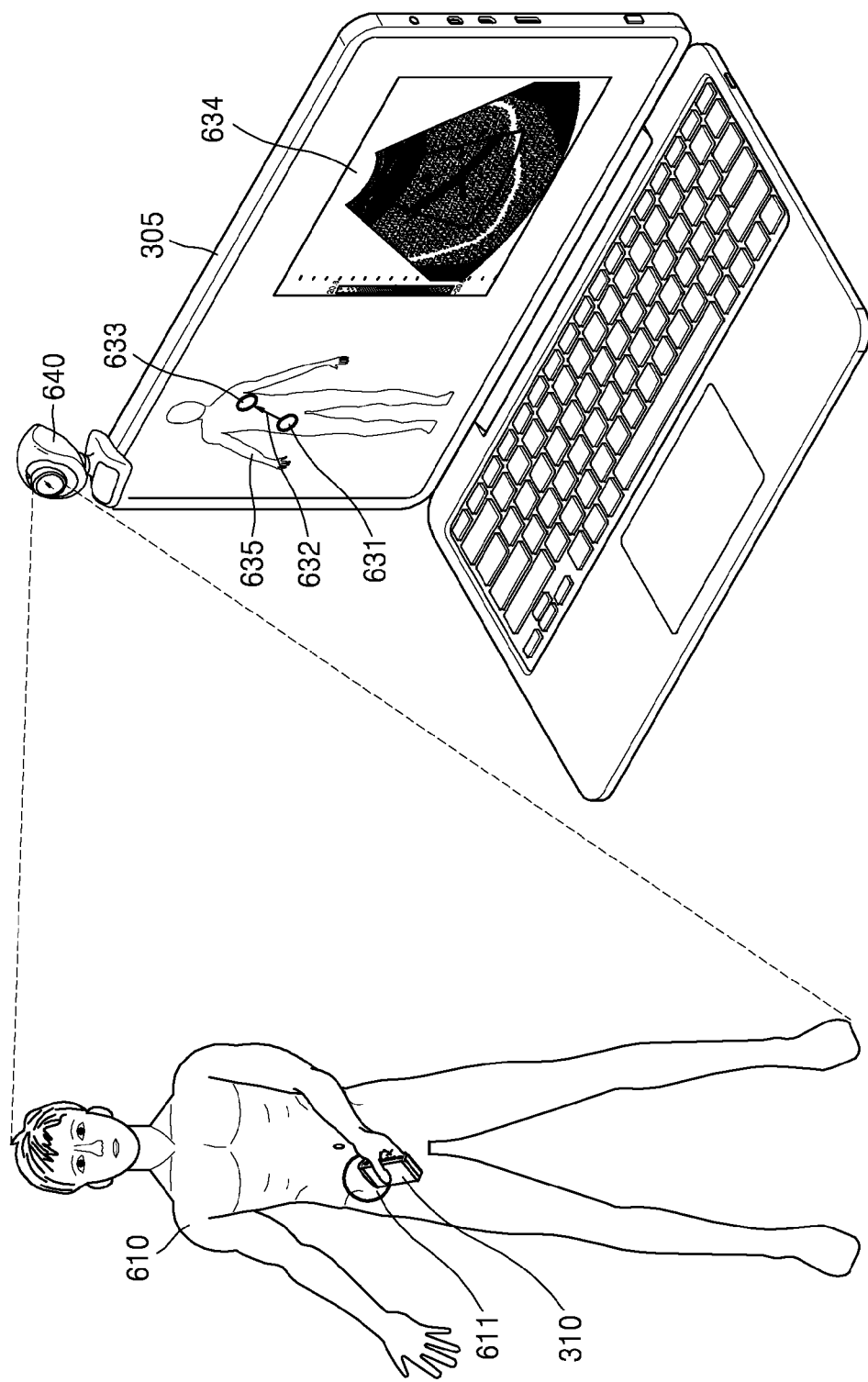
[Fig. 7]

[Fig. 8A]
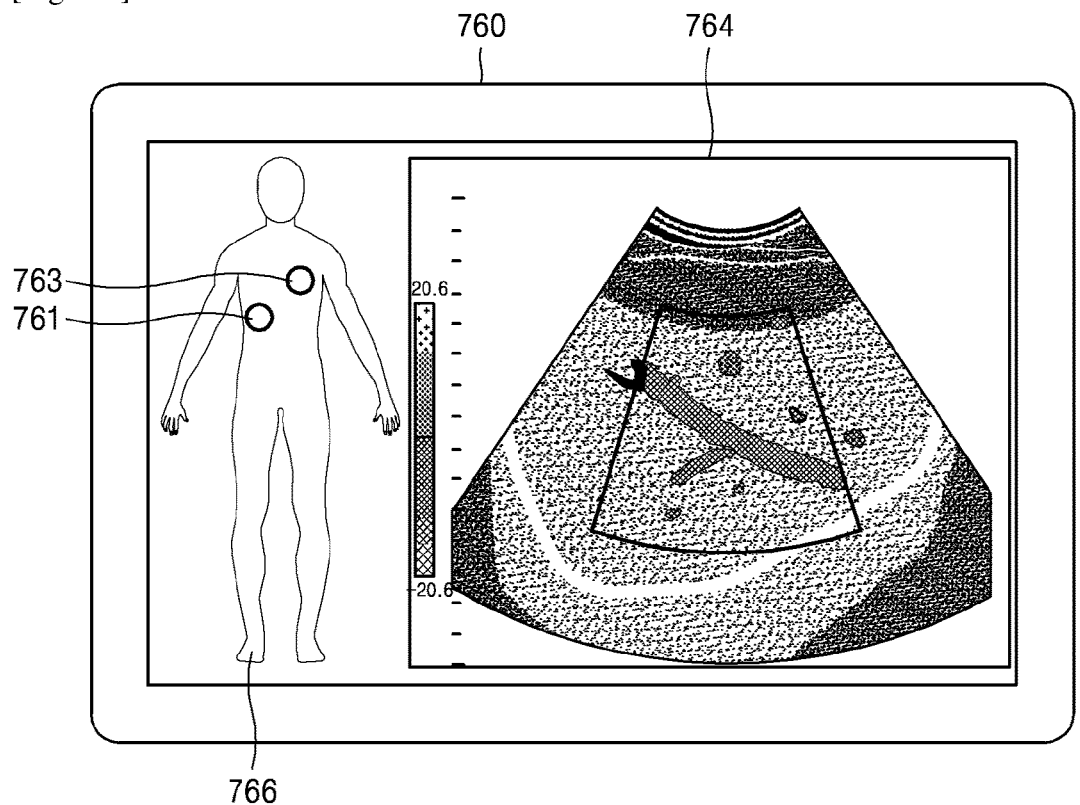
[Fig. 8B]
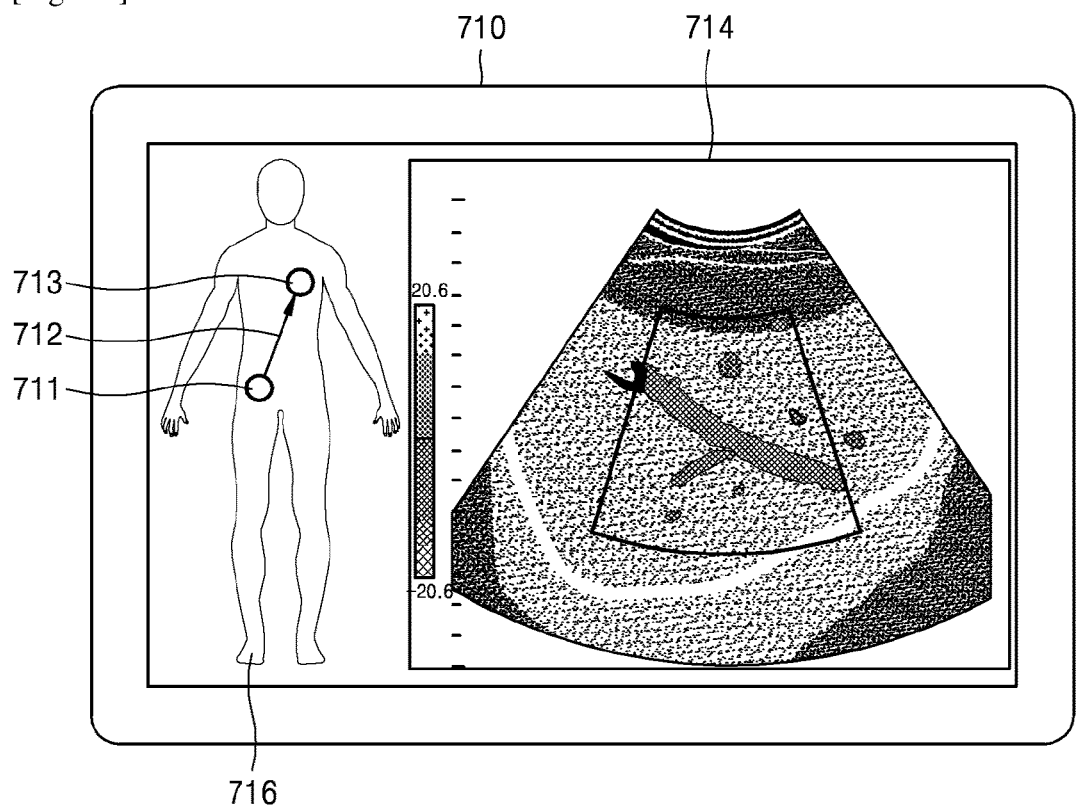

[Fig. 9A]
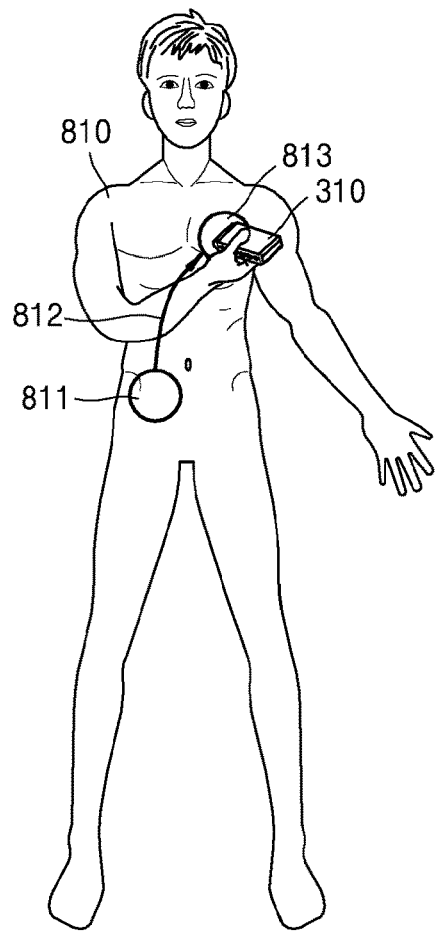
[Fig. 9B]
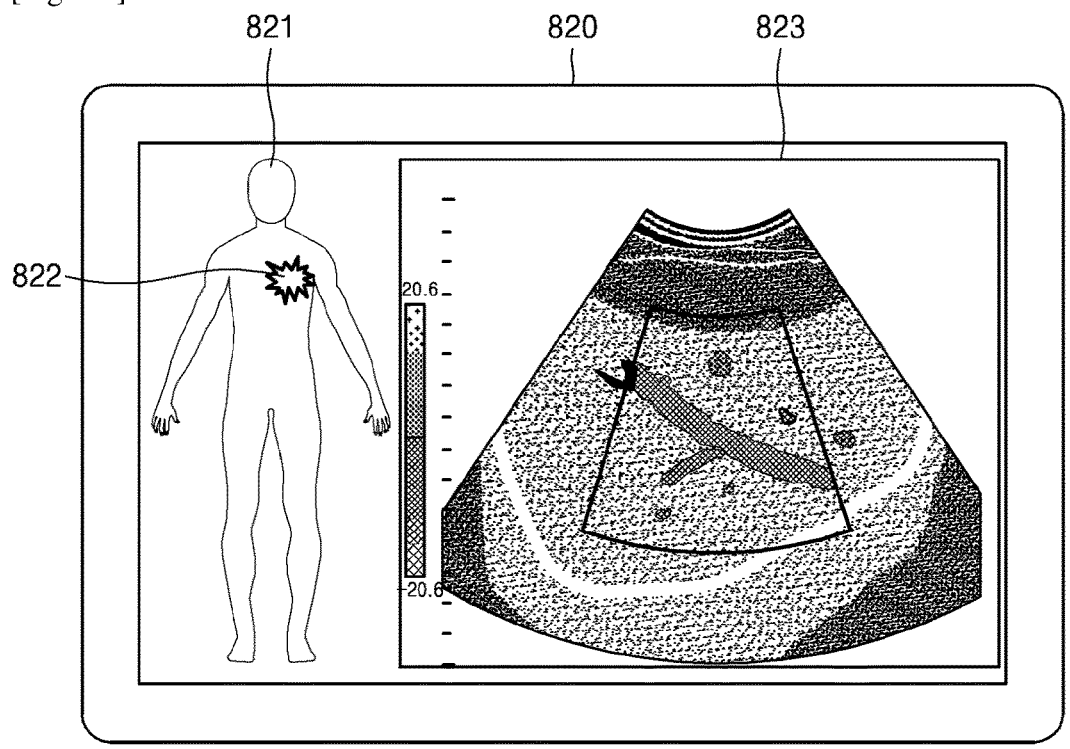

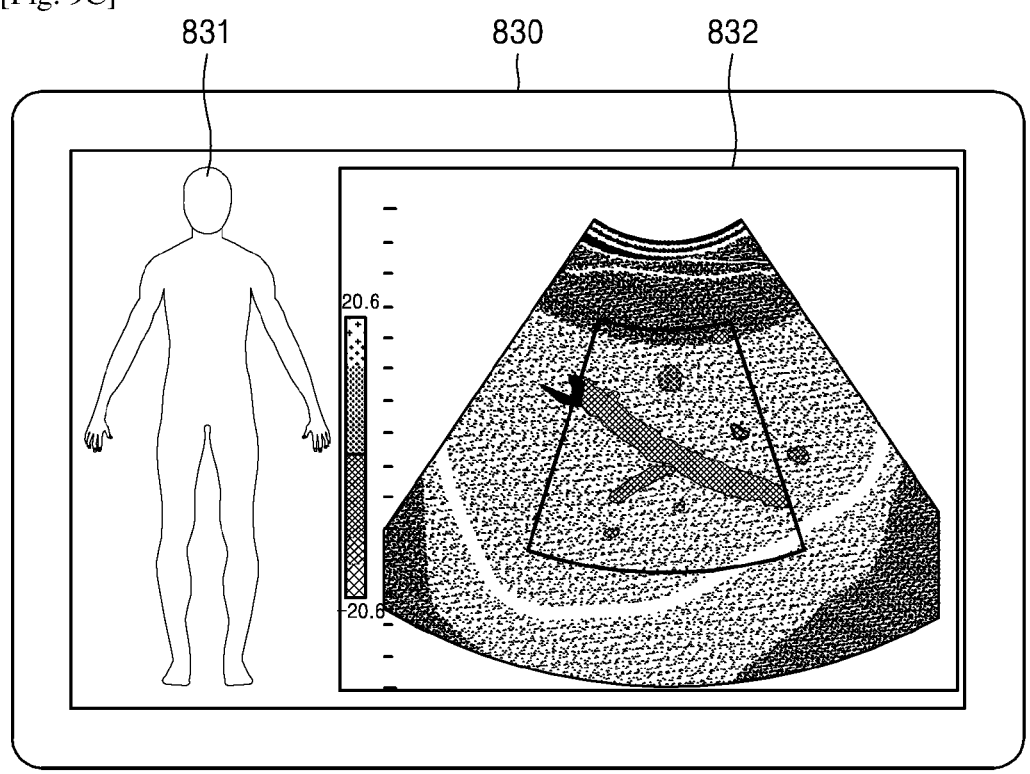
[Fig. 9C]

[Fig. 10A]
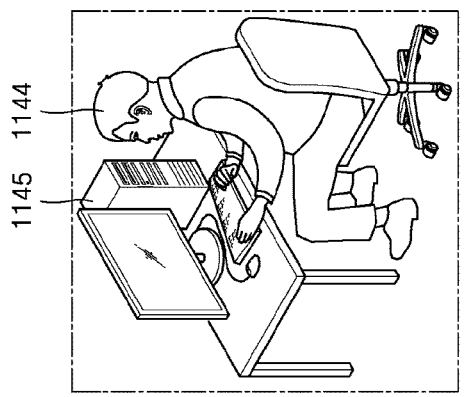
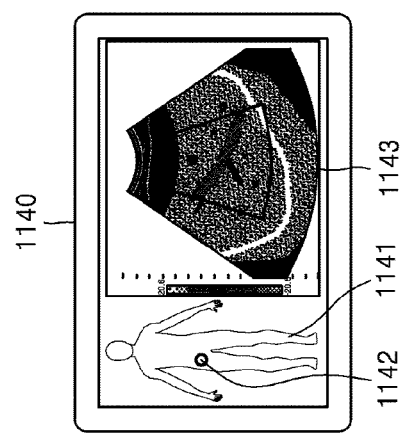
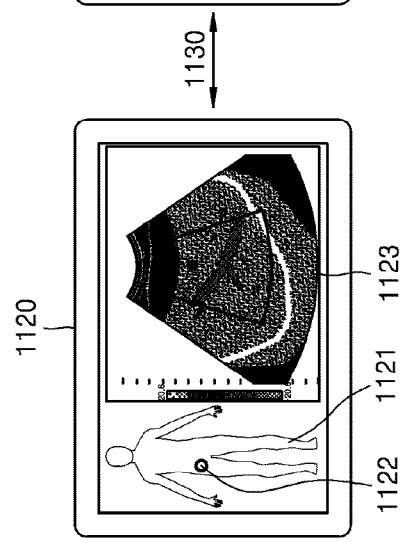
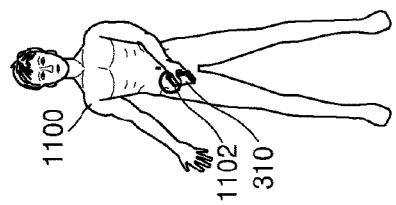

[Fig. 10B]
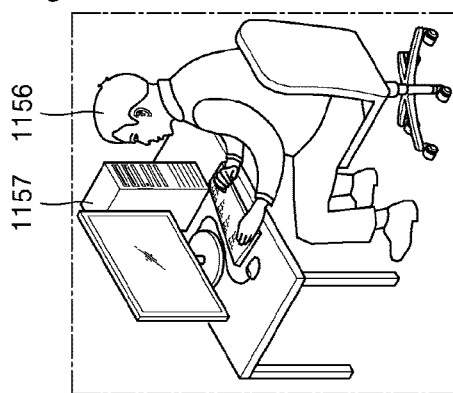
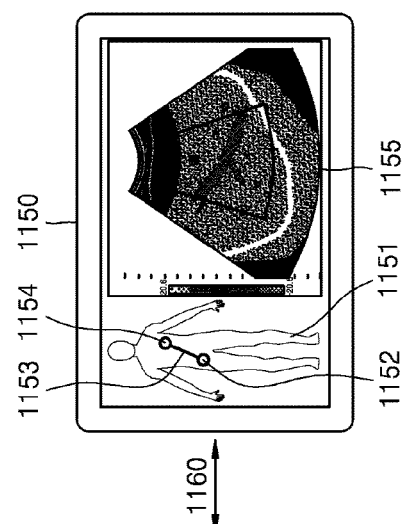
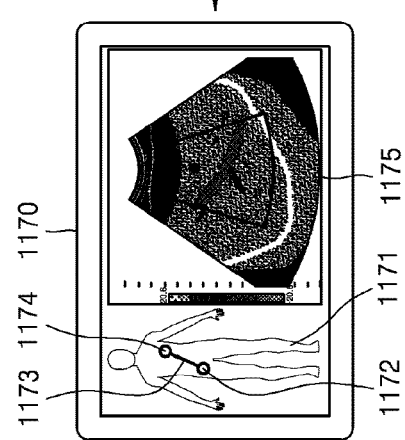
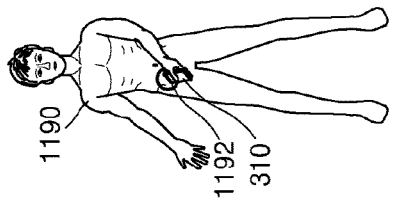

[Fig. 11]
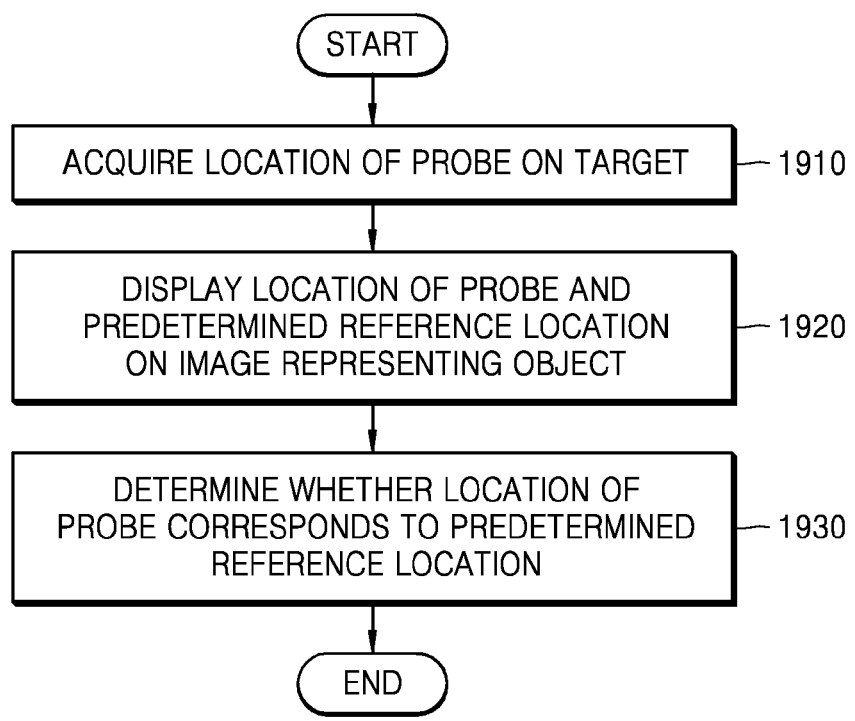

[Fig. 12]
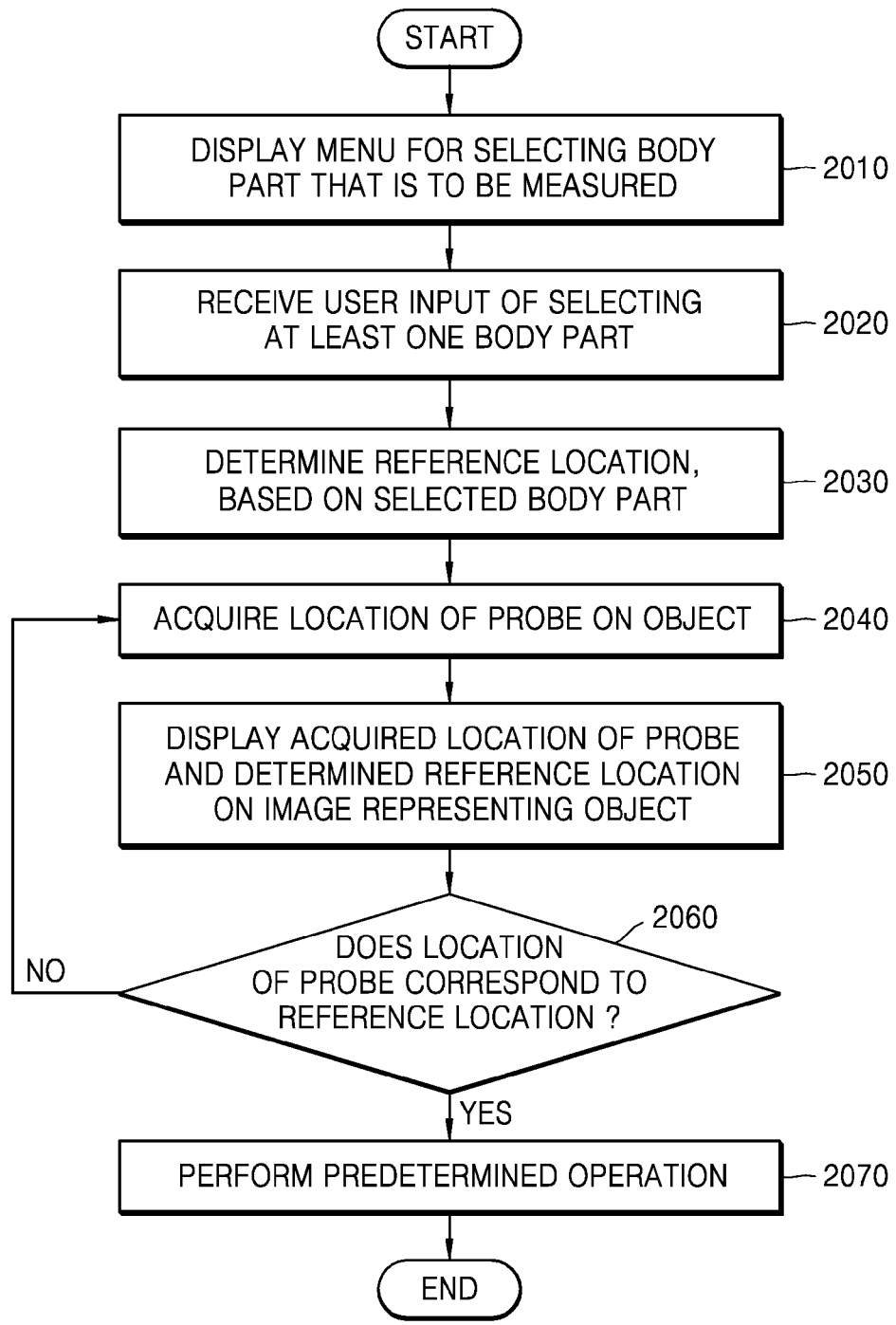

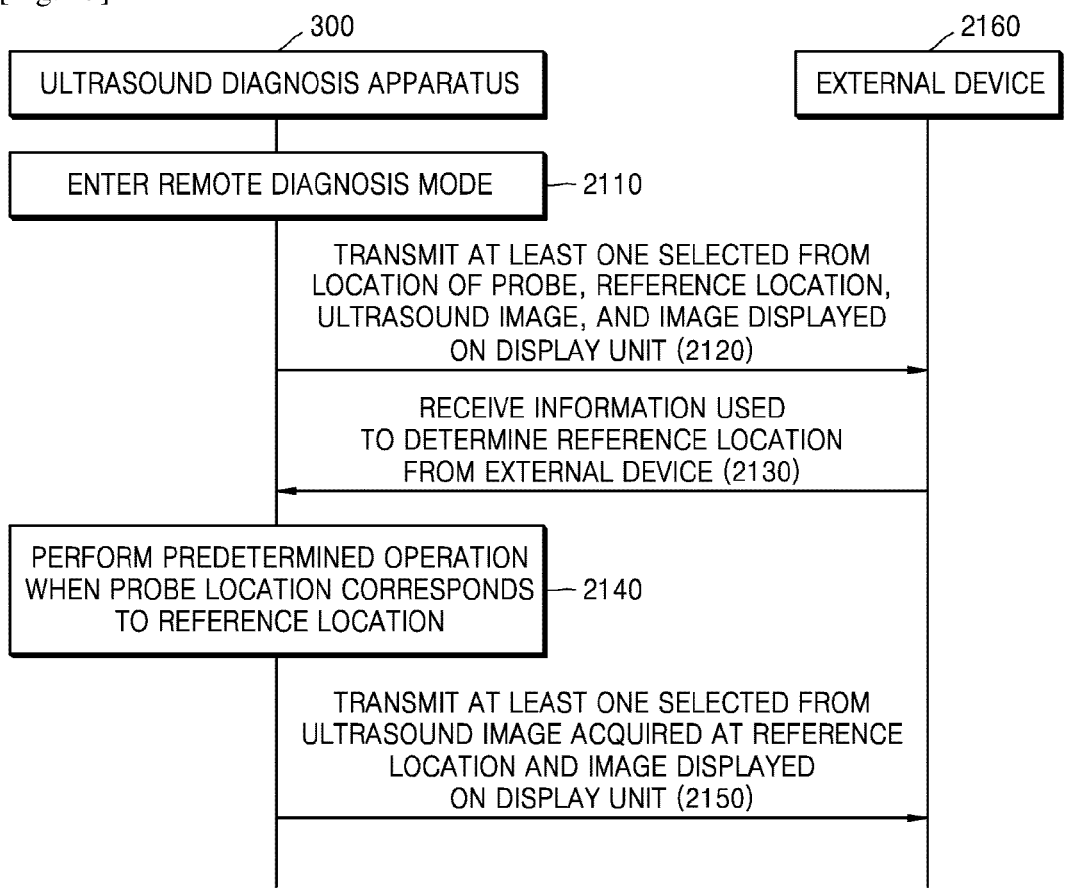
[Fig. 13]

[Fig. 14]
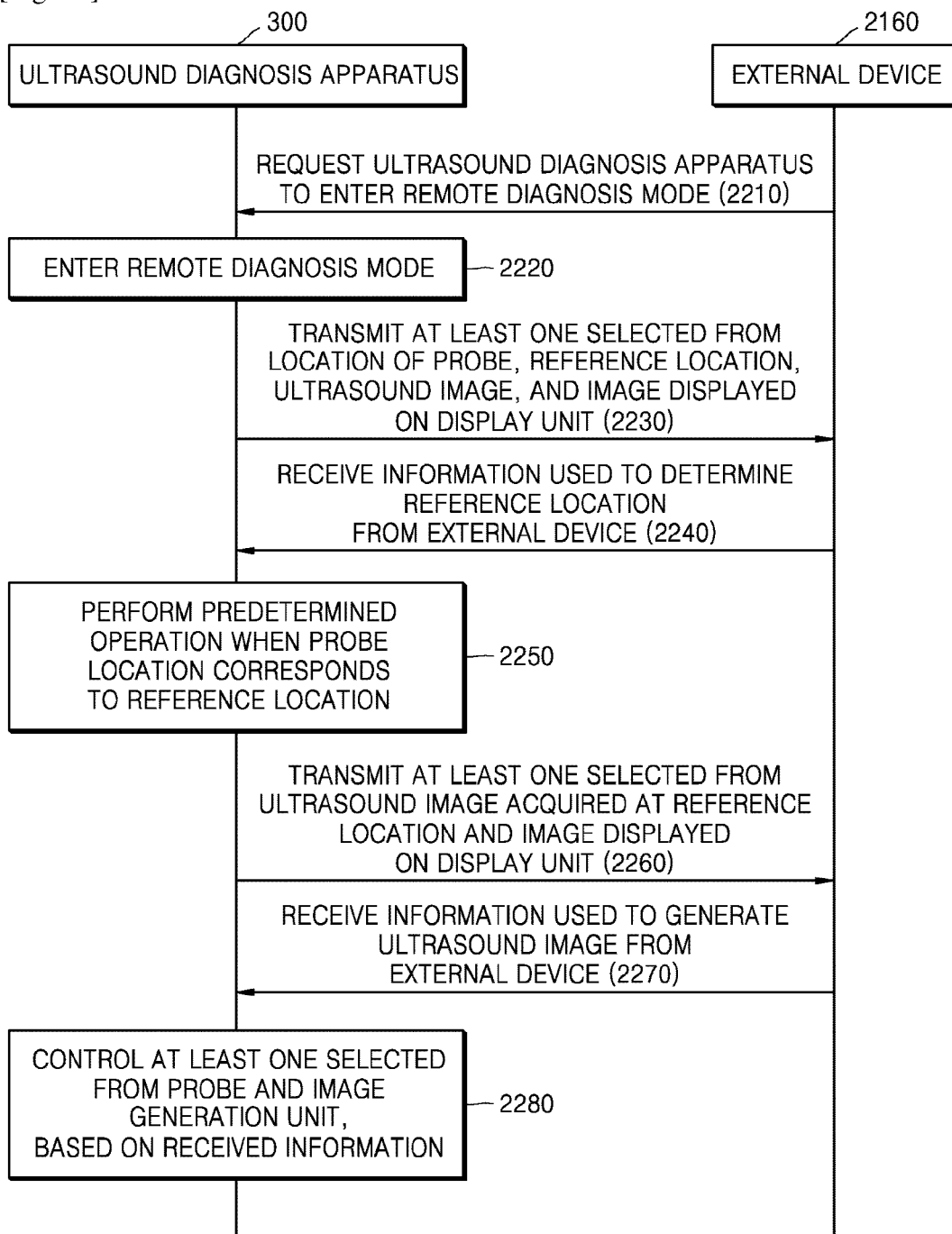

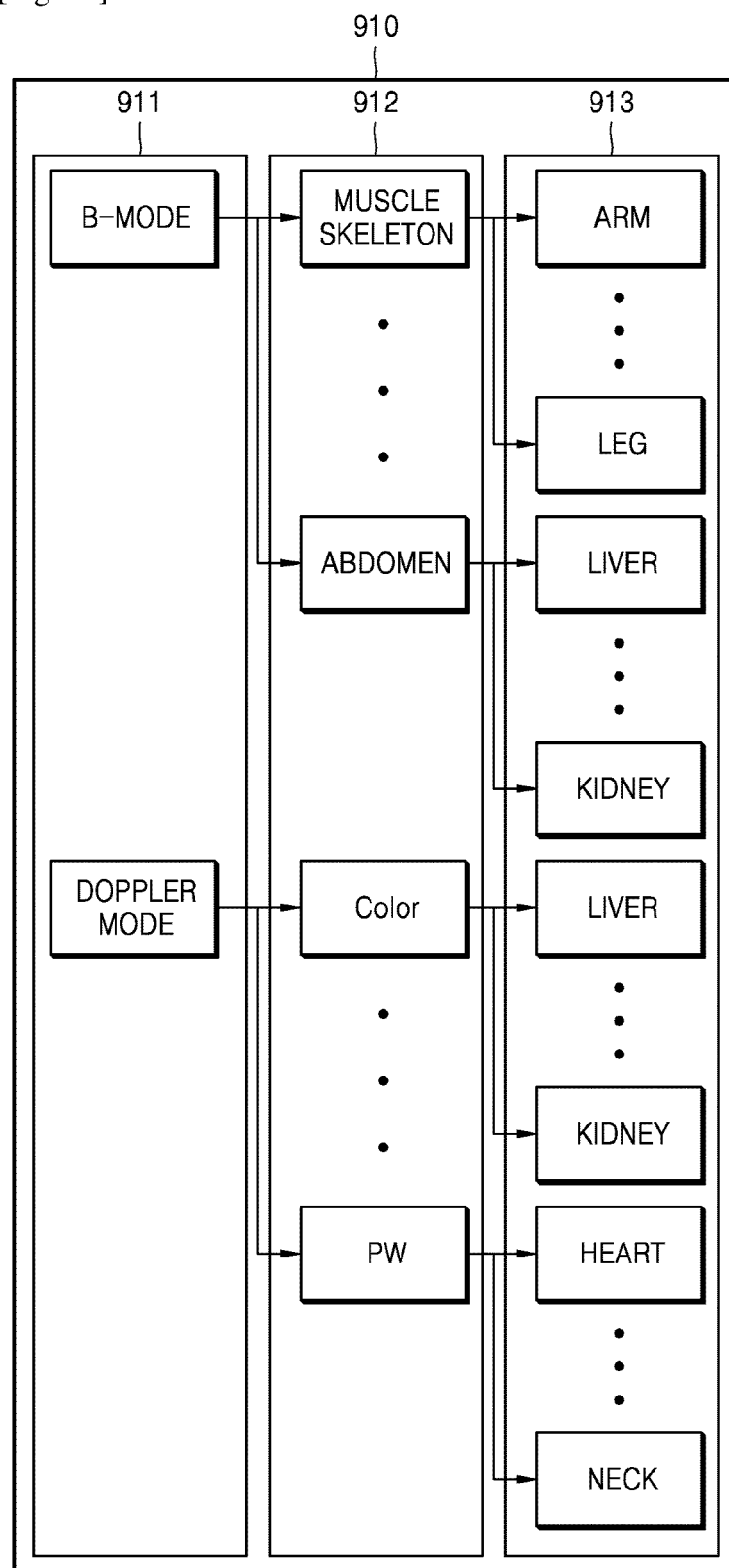
[Fig. 15]

[Fig. 16]
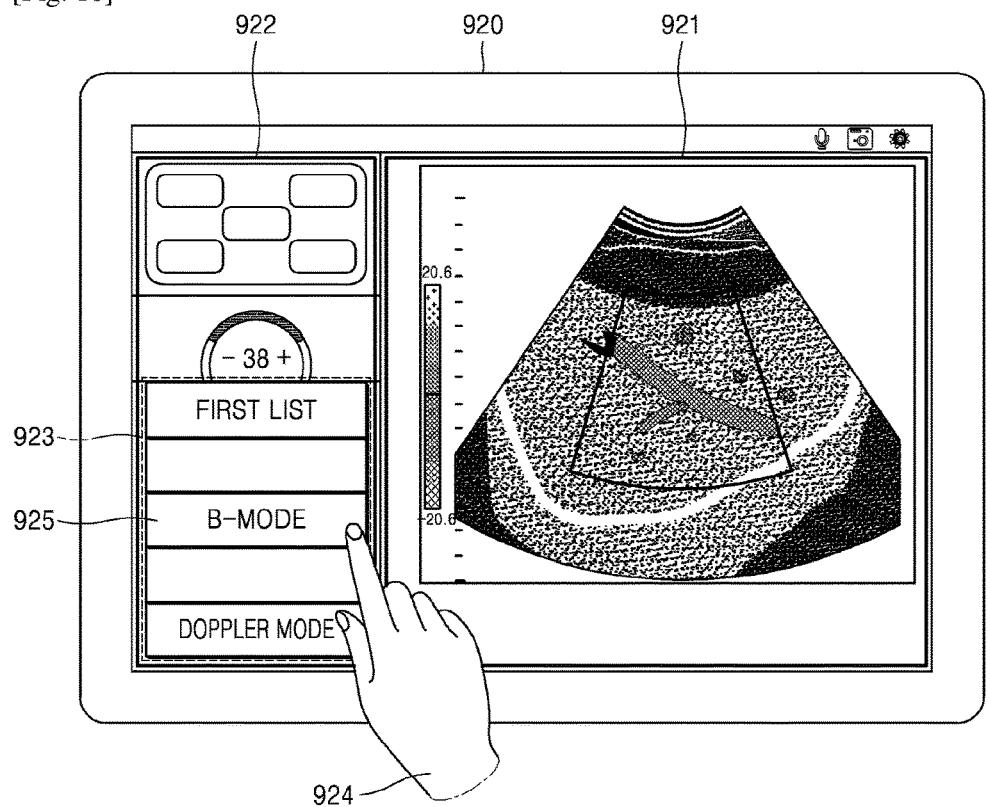
[Fig. 17]
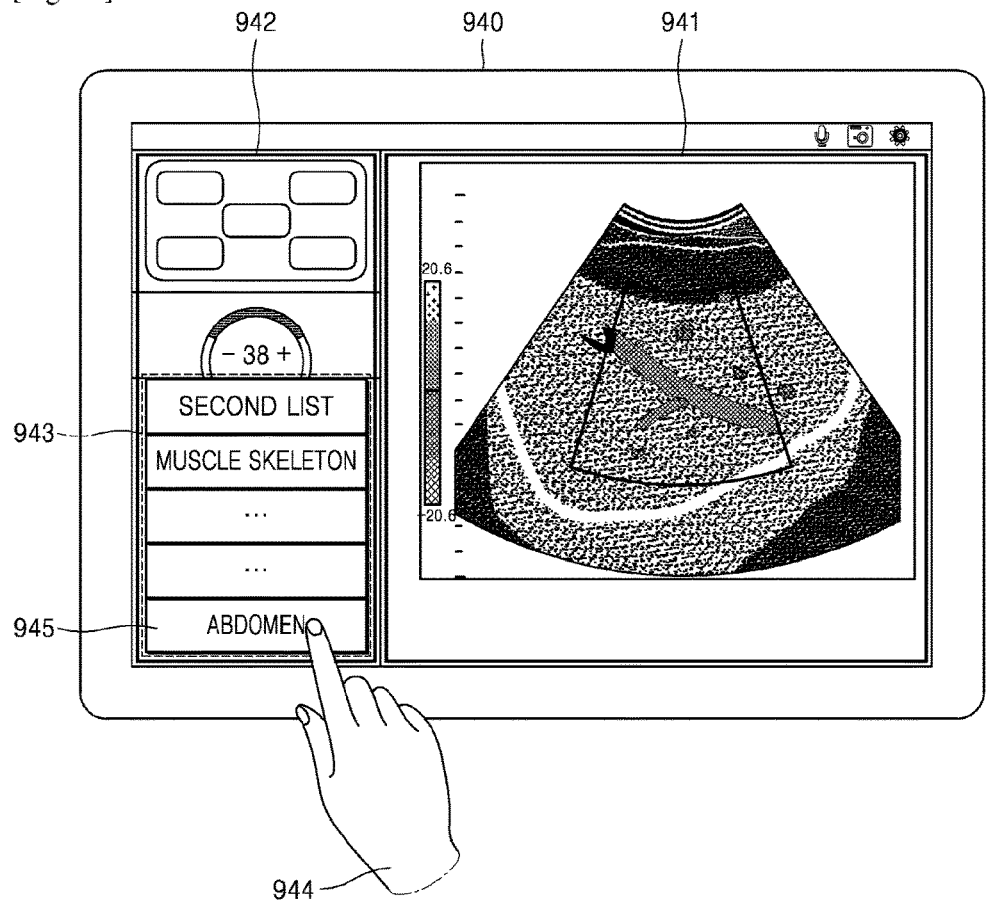

[Fig. 18]
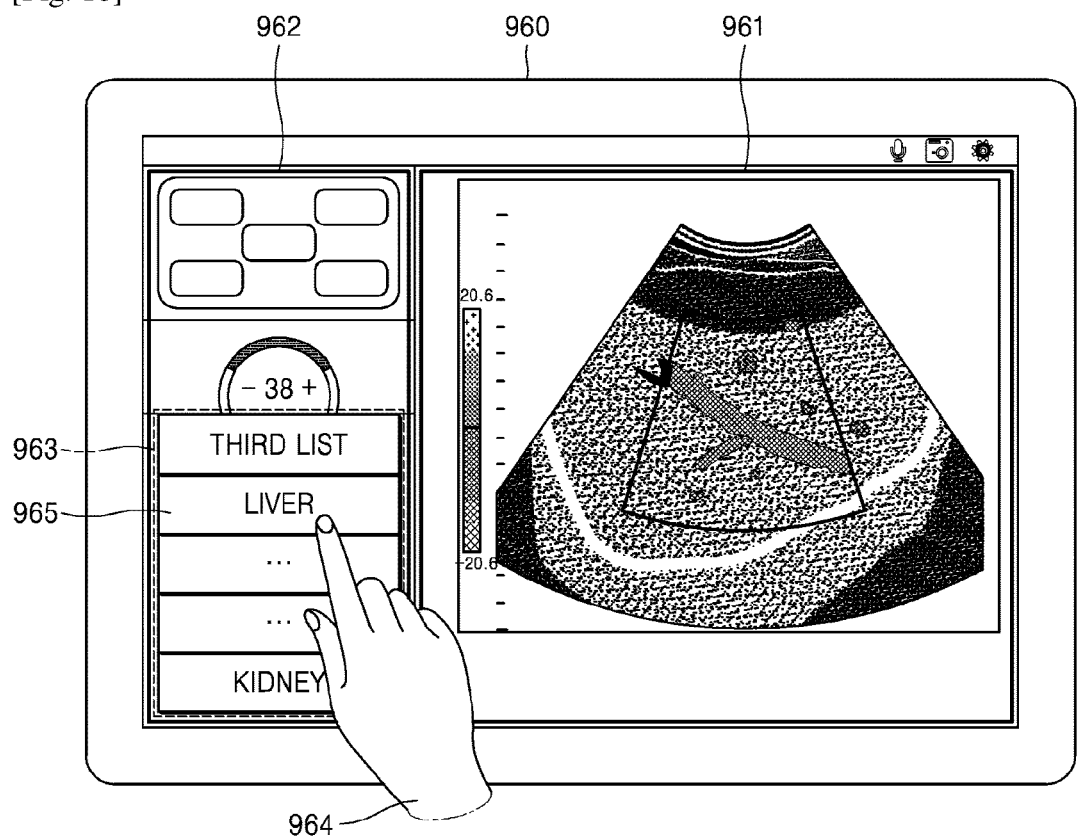

[Fig. 19]
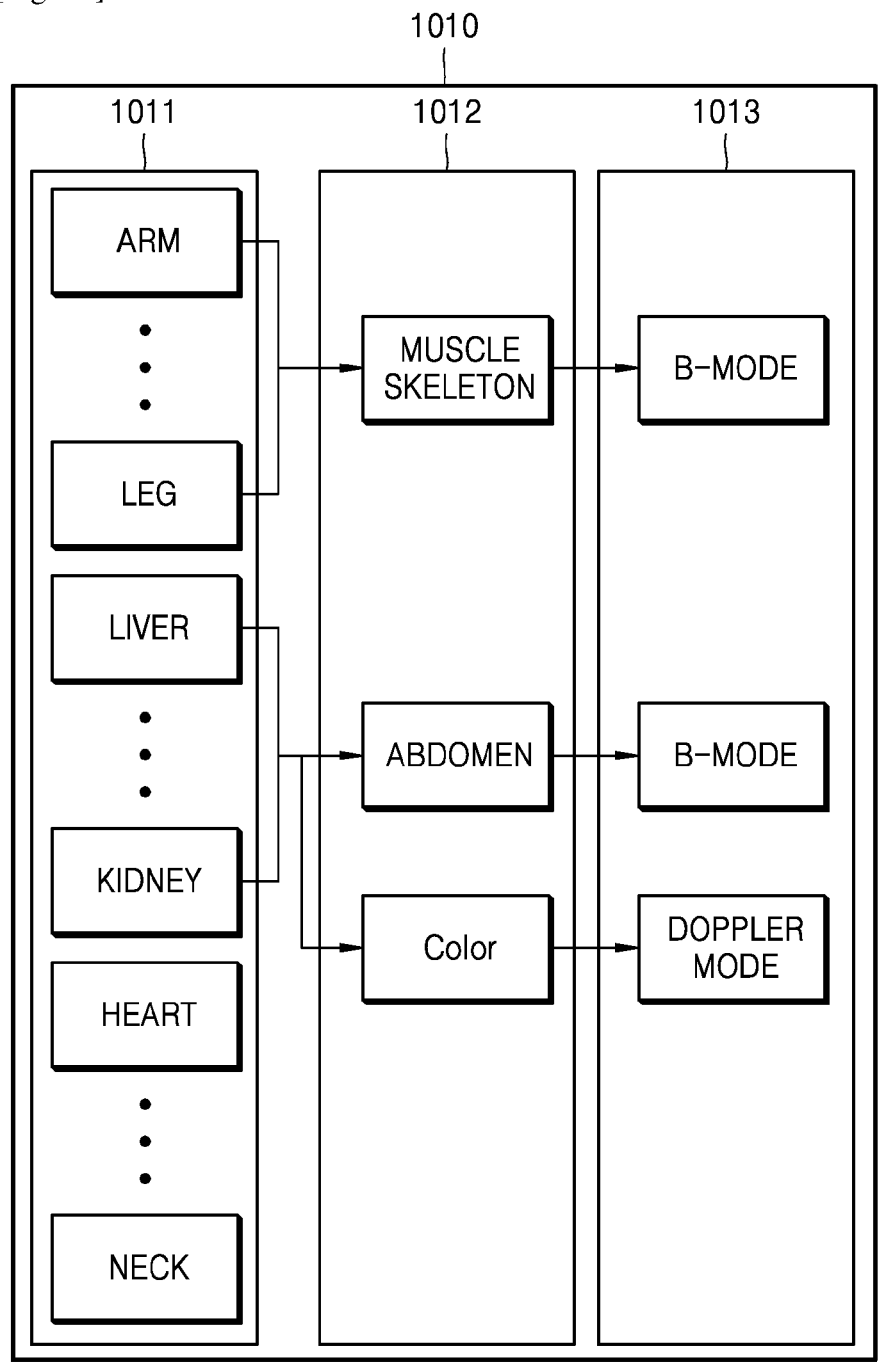

[Fig. 20]
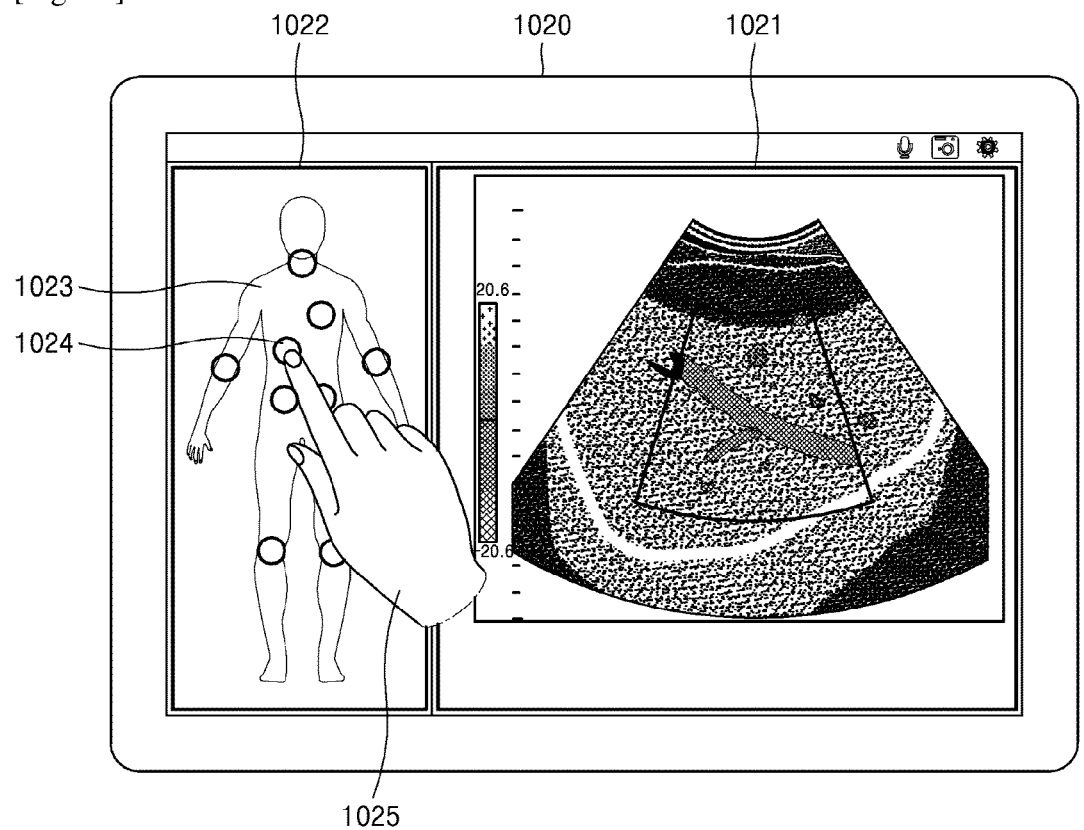
[Fig. 21]
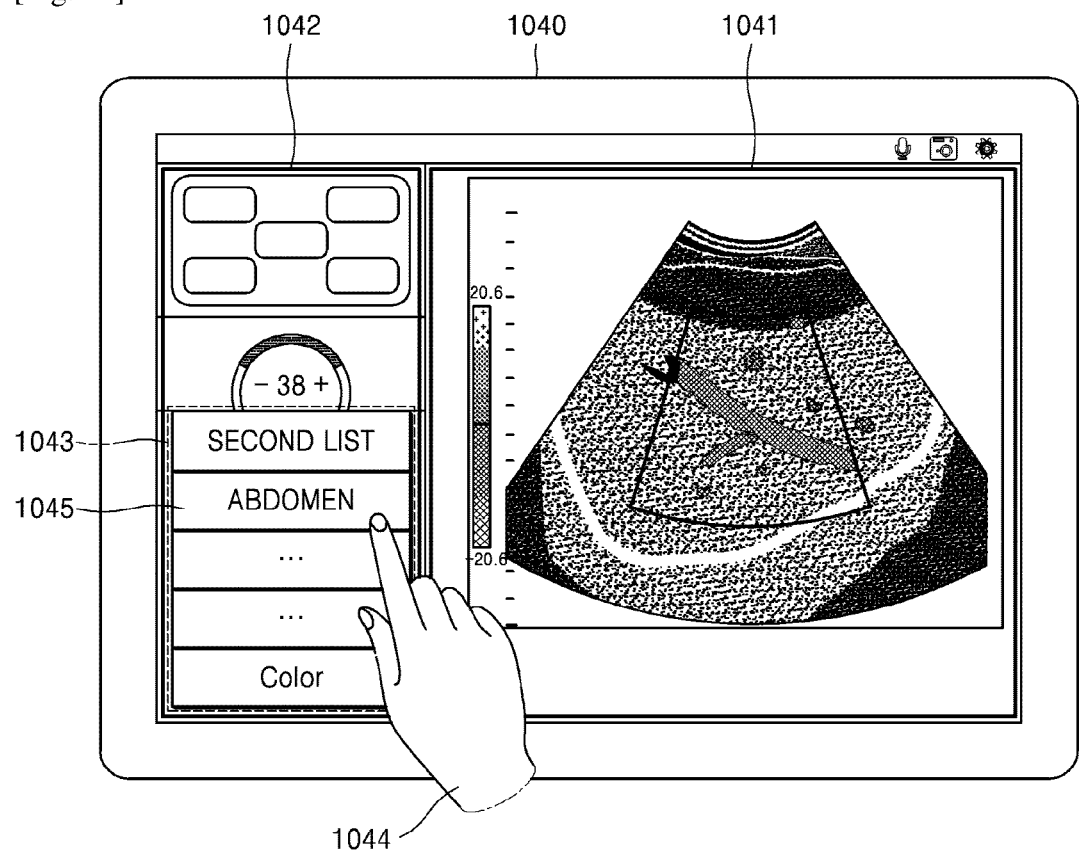

[Fig. 22]
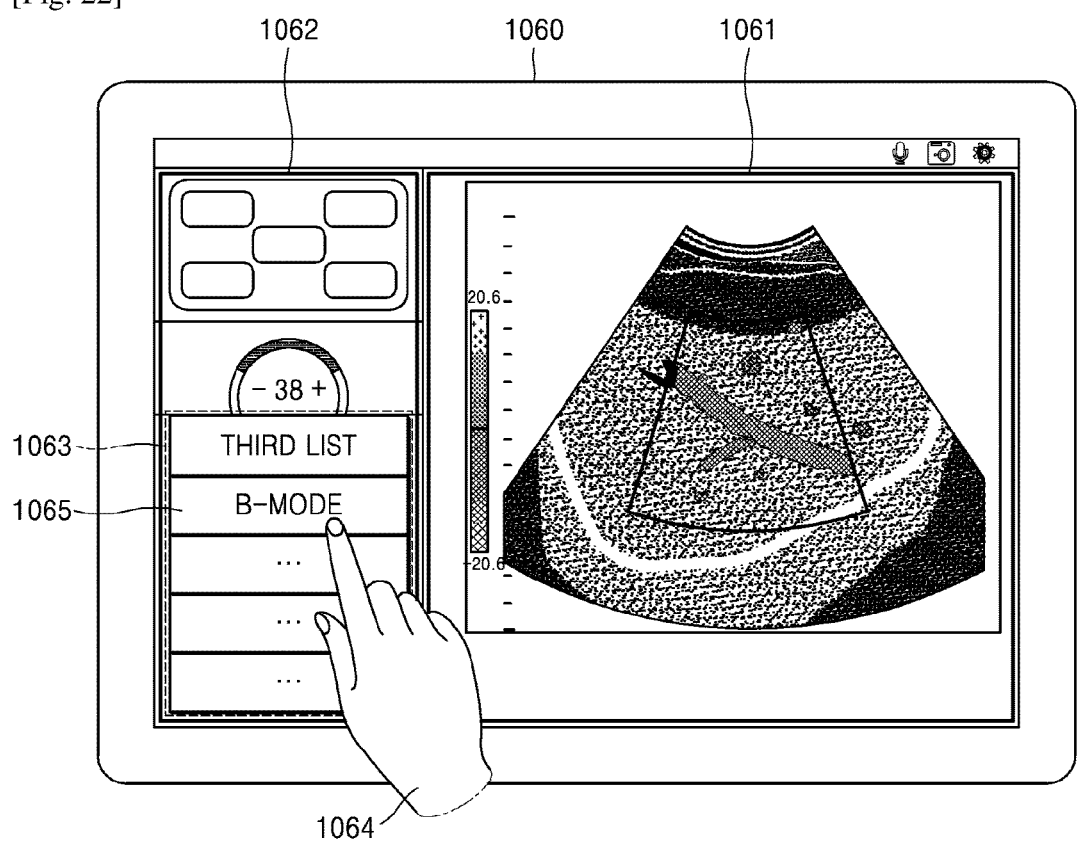

ULTRASOUND DIAGNOSIS APPARATUS FOR SELF-DIAGNOSIS AND REMOTE-DIAGNOSIS, AND METHOD OF OPERATING THE ULTRASOUND DIAGNOSIS APPARATUS

TECHNICAL FIELD

One or more exemplary embodiments relate to an ultrasound diagnosis apparatus and a method of operating the ultrasound diagnosis apparatus. More particularly, one or more exemplary embodiments relate to an ultrasound diagnosis apparatus which a user may use to conveniently acquire an ultrasound image at home even when he or she is unskilled at using the ultrasound diagnosis apparatus, and an ultrasound diagnosis method of conveniently acquiring an ultrasound image at a user's home by using the ultrasound diagnosis apparatus. One or more exemplary embodiments also relate to an ultrasound diagnosis apparatus and method in which an ultrasound image acquired by the ultrasound diagnosis apparatus is transmitted to a skilled user remotely located away from the ultrasound diagnosis apparatus so that the ultrasound image may be used in diagnosis.

BACKGROUND ART

Ultrasound diagnosis apparatuses transmit an ultrasound signal generated by a transducer of a probe to an object and receive information regarding an ultrasound echo signal reflected from the object, thereby obtaining an image of a part inside the object. In particular, ultrasound diagnosis apparatuses are used for medical purposes, such as observation of the inside of an object, detection of foreign substances inside the object, and diagnosis of damage thereof. Such ultrasound diagnosis apparatuses have various advantages, including stability, real-time display, and safety because there is no exposure to radiation, compared to X-ray apparatuses, and thus, the ultrasound diagnosis apparatuses are commonly used together with other image diagnosis apparatuses.

In this connection, an ultrasound diagnosis apparatus and method enabling a user to easily acquire an ultrasound image even when the user is not skilled in ultrasound diagnosis apparatuses need to be provided.

DISCLOSURE OF INVENTION

Technical Problem

Since ultrasound diagnosis apparatuses are large and expensive equipment, general users other than skilled persons working for professional organizations have difficulty in utilizing the ultrasound diagnosis apparatuses. However, ultrasound diagnosis apparatuses have currently become miniaturized with developments in technology, and prices of ultrasound diagnosis apparatuses have reached low enough levels for general users to purchase the ultrasound diagnosis apparatuses. When a general user utilizes an ultrasound diagnosis apparatus, he or she can obtain an ultrasound image at home. Thus, even general users can simply observe the inside of their bodies and can be diagnosed remotely by providing acquired ultrasound images to a remote skilled user. However, since it is difficult to manipulate ultrasound diagnosis apparatuses, if a user has no background knowledge, it is difficult to position a probe at a body part that is to be measured, and it is also difficult to set suitable image modes according to body parts. In other words, since general users are not provided with an interface that can be easily used by the general users, availability of ultrasound diagnosis apparatuses degrades.

One or more exemplary embodiments include an ultrasound diagnosis apparatus and method enabling general users to easily acquire ultrasound images even when the users have no background knowledge, and a computer-readable storage medium having the ultrasound diagnosis method recorded thereon.

Additional aspects will be set forth in part in the description which follows and, in part, will be apparent from the description, or may be learned by practice of the presented embodiments.

Solution to Problem

According to one or more embodiments of the present invention, an ultrasound diagnosis apparatus includes a probe configured to acquire ultrasound data of an object; an image generation unit configured to generate an ultrasound image of the object by using the ultrasound data; a probe location acquisition unit configured to acquire a location of the probe on the object; a display unit configured to display the location of the probe and a reference location on an image representing the object; and a control unit configured to determine whether the location of the probe corresponds to the reference location.

The ultrasound diagnosis apparatus may further include a storage unit configured to map a plurality of locations of the probe with a plurality of reference ultrasound images and store a result of the mapping. The probe location acquisition unit may compare the ultrasound image with the plurality of reference ultrasound images, select one from among the plurality of reference ultrasound images based on a result of the comparison, and acquire a location corresponding to the selected reference ultrasound image as the location of the probe.

The ultrasound diagnosis apparatus may further include a photographing unit configured to photograph the probe and the object. The probe location acquisition unit may detect an area corresponding to the probe and an area corresponding to the object from an image captured by photographing the probe and the object, and acquire the location of the probe based on a location of the area corresponding to the probe with respect to the area corresponding to the object.

When it is determined that the location of the probe does not correspond to the reference location, the control unit may determine a movement path to be taken by the probe to move to the reference location, and the display unit may display the movement path from the location of the probe to the reference location on the image representing the object.

When the location of the probe corresponds to the reference location, the control unit may control the display unit to display an image representing that the location of the probe corresponds to the reference location.

When the location of the probe corresponds to the reference location, the control unit may control the probe to transmit an ultrasound signal to the object and receive an echo signal from the object to acquire the ultrasound data.

The ultrasound diagnosis apparatus may further include a communication unit configured to transmit the ultrasound image to an external device when the location of the probe corresponds to the reference location.

The ultrasound diagnosis apparatus may further include an input unit configured to receive a user input of selecting at least one location from among a plurality of locations on the object, and the control unit may determine the selected location as the reference location.

The ultrasound diagnosis apparatus may further include a communication unit configured to receive, from an external device, information that is used to determine the reference location, and the control unit may determine the reference location based on the received information.

The ultrasound diagnosis apparatus may further include a communication unit configured to transmit at least one selected from the location of the probe, the reference location, the ultrasound image, and an image displayed on the display unit to an external device.

The communication unit may receive information that is used to generate the ultrasound image, from the external device. The control unit may control at least one selected from the probe and the image generation unit, based on the received information.

According to one or more embodiments of the present invention, a method of operating an ultrasound diagnosis apparatus including a probe acquiring ultrasound data of an object and an image generation unit generating an ultrasound image of the object by using the ultrasound data includes acquiring a location of the probe on the object; displaying the location of the probe and a reference location on an image representing the object; and determining whether the location of the probe corresponds to the reference location.

The method may further include mapping a plurality of locations of the probe with a plurality of reference ultrasound images and storing a result of the mapping. The acquiring of the location of the probe may include comparing the ultrasound image with the plurality of reference ultrasound images; selecting one reference ultrasound image from the plurality of reference ultrasound images, based on a result of the comparing; and acquiring a location corresponding to the selected reference ultrasound image as the location of the probe.

The method may further include photographing the probe and the object, and the acquiring of the location of the probe may include detecting an area corresponding to the probe and an area corresponding to the object from an image captured by photographing the probe and the object; and acquiring the location of the probe based on a location of the area corresponding to the probe with respect to the area corresponding to the object.

The determining whether the location of the probe corresponds to the reference location may include determining a movement path to be taken by the probe to move to the reference location when it is determined that the location of the probe does not correspond to the reference location; and displaying the movement path from the location of the probe to the reference location on the image representing the object.

The method may further include displaying an image representing that the location of the probe corresponds to the reference location, when the location of the probe corresponds to the reference location.

The method may further include transmitting an ultrasound signal to the object and receiving an echo signal from the object to acquire the ultrasound data, when it is determined that the location of the probe corresponds to the reference location.

The method may further include transmitting the ultrasound image of the object to an external device when it is determined that the location of the probe corresponds to the reference location.

The method may further include receiving a user input of selecting at least one location from among a plurality of locations on the object; and determining the selected location as the reference location.

The method may further include receiving, from an external device, information that is used to determine the reference location; and determining the reference location based on the received information.

The method may further include transmitting at least one selected from the location of the probe, the reference location, the ultrasound image, and an image displayed on display unit to an external device.

The method may further include receiving information that is used to generate the ultrasound image, from the external device; and controlling at least one selected from the probe and the image generation unit, based on the received information.

According to one or more embodiments of the present invention, a non-transitory computer-readable recording medium has recorded thereon a program for executing the above-described method.

BRIEF DESCRIPTION OF DRAWINGS

These and/or other aspects will become apparent and more readily appreciated from the following description of the embodiments, taken in conjunction with the accompanying drawings in which:

FIG. 1 is a block diagram of an ultrasound diagnosis apparatus according to an exemplary embodiment of the present disclosure;

FIG. 2 is a block diagram of a wireless probe according to an exemplary embodiment of the present disclosure;

FIG. 3 schematically illustrates an ultrasound diagnosis apparatus being used by a user according to an exemplary embodiment of the present disclosure;

FIG. 4 is a block diagram of an ultrasound diagnosis apparatus according to an exemplary embodiment of the present disclosure;

FIG. 5 is a block diagram of an ultrasound diagnosis apparatus according to an exemplary embodiment of the present disclosure;

FIGS. 6A and 6B explain a method in which an ultrasound diagnosis apparatus operates, according to an exemplary embodiment of the present disclosure;

FIG. 7 explains a method in which an ultrasound diagnosis apparatus operates, according to an exemplary embodiment of the present disclosure;

FIGS. 8A and 8B illustrate screen images of an ultrasound diagnosis apparatus according to an exemplary embodiment of the present disclosure;

FIGS. 9A-9C explain a method in which an ultrasound diagnosis apparatus operates, according to an exemplary embodiment of the present disclosure;

FIGS. 10A and 10B explain a method in which an ultrasound diagnosis apparatus interoperates with an external device, according to an exemplary embodiment of the present disclosure;

FIG. 11 is a flowchart of a method of operating an ultrasound diagnosis apparatus, according to an exemplary embodiment of the present disclosure;

FIG. 12 is a flowchart of a method of operating an ultrasound diagnosis apparatus in order to determine a reference location, according to an exemplary embodiment of the present disclosure;

FIG. 13 is a process flow diagram of a method in which an ultrasound diagnosis apparatus interoperates with an external device, according to an exemplary embodiment of the present disclosure;

FIG. 14 is a process flow diagram of a method in which an ultrasound diagnosis apparatus interoperates with an external device, according to an exemplary embodiment of the present disclosure;

FIG. 15 explains a menu that may be provided when a user skilled at using ultrasound diagnosis apparatuses uses an ultrasound diagnosis apparatus;

FIG. 16 explains a menu that may be provided when a user skilled at using ultrasound diagnosis apparatuses uses an ultrasound diagnosis apparatus;

FIG. 17 explains a menu that may be provided when a user skilled at using ultrasound diagnosis apparatuses uses an ultrasound diagnosis apparatus;

FIG. 18 explains a menu that may be provided when a user skilled at using ultrasound diagnosis apparatuses uses an ultrasound diagnosis apparatus;

FIG. 19 explains a menu that may be provided when a user unskilled at using ultrasound diagnosis apparatuses uses an ultrasound diagnosis apparatus;

FIG. 20 explains a menu that may be provided when a user unskilled at using ultrasound diagnosis apparatuses uses an ultrasound diagnosis apparatus;

FIG. 21 explains a menu that may be provided when a user unskilled at using ultrasound diagnosis apparatuses uses an ultrasound diagnosis apparatus; and FIG. 22 explains a menu that may be provided when a user unskilled at using ultrasound diagnosis apparatuses uses an ultrasound diagnosis apparatus.

MODE FOR THE INVENTION

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Also, a "user" may be, but is not limited to, a medical expert such as a doctor, a nurse, a medical laboratory technologist, a medial image expert, or a technician who repairs a medical apparatus. Hereinafter, exemplary embodiments will be described in detail with reference to the accompanying drawings.

FIG. 1 is a block diagram showing a configuration of an ultrasound diagnosis apparatus according to an embodiment.

Referring to FIG. 1, the ultrasound diagnosis apparatus 100 may include a probe 2, an ultrasound transceiver 10, an image processor 20, a communication module 30, a display 300, a memory 40, an input device 50, and a controller 60, which may be connected to one another via buses 70.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 2 transmits ultrasound waves to an object 1 in response to a driving signal applied by the ultrasound transceiver 10 and receives echo signals reflected by the object 1. The probe 2 includes a plurality of transducers, and the plurality of transducers oscillate in response to electric signals and generate acoustic energy, that is, ultrasound waves. Furthermore, the probe 2 may be connected to the main body of the ultrasound diagnosis apparatus 100 by wire or wirelessly, and according to embodiments, the ultrasound diagnosis apparatus 100 may include a plurality of probes 2.

A transmitter 11 supplies a driving signal to the probe 2. The transmitter 110 includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 delays the pulses by delay times necessary for determining transmission directionality. The pulses which have been delayed correspond to a plurality of piezoelectric vibrators included in the probe 2, respectively. The pulser 19 applies a driving signal (or a driving pulse) to the probe 2 based on timing corresponding to each of the pulses which have been delayed.

A receiver 12 generates ultrasound data by processing echo signals received from the probe 2. The receiver 120 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion with respect to the amplified echo signals. The reception delaying unit 15 delays digital echo signals output by the ADC 1124 by delay times necessary for determining reception directionality, and the summing unit 16 generates ultrasound data by summing the echo signals processed by the reception delaying unit 15. In some embodiments, the receiver 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transceiver 10 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 22 extracts B mode components from ultrasound data and processes the B mode components. An image generator 24 may generate an ultrasound image indicating signal intensities as brightness based on the extracted B mode components 22.

Similarly, a Doppler processor 23 may extract Doppler components from ultrasound data, and the image generator 24 may generate a Doppler image indicating a movement of an object as colors or waveforms based on the extracted Doppler components.

According to an embodiment, the image generator 24 may generate a three-dimensional (3D) ultrasound image via volume-rendering with respect to volume data and may also generate an elasticity image by imaging deformation of the object 1 due to pressure. Furthermore, the image generator 24 may display various pieces of additional information in an ultrasound image by using text and graphics. In addition, the generated ultrasound image may be stored in the memory 40.

A display 25 displays the generated ultrasound image. The display 25 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 25 according to embodiments.

The communication module 30 is connected to a network 3 by wire or wirelessly to communicate with an external device or a server. The communication module 30 may exchange data with a hospital server or another medical apparatus in a hospital, which is connected thereto via a PACS. Furthermore, the communication module 30 may perform data communication according to the digital imaging and communications in medicine (DICOM) standard.

The communication module 30 may transmit or receive data related to diagnosis of an object, e.g., an ultrasound image, ultrasound data, and Doppler data of the object, via the network 3 and may also transmit or receive medical images captured by another medical apparatus, e.g., a computed tomography (CT) apparatus, a magnetic resonance imaging (MRI) apparatus, or an X-ray apparatus. Furthermore, the communication module 30 may receive information about a diagnosis history or medical treatment schedule of a patient from a server and utilizes the received information to diagnose the patient. Furthermore, the communication module 30 may perform data communication not only with a server or a medical apparatus in a hospital, but also with a portable terminal of a medical doctor or patient.

The communication module 30 is connected to the network 3 by wire or wirelessly to exchange data with a server 35, a medical apparatus 34, or a portable terminal 36. The communication module 30 may include one or more components for communication with external devices. For example, the communication module 1300 may include a local area communication module 31, a wired communication module 32, and a mobile communication module 33.

The local area communication module 31 refers to a module for local area communication within a predetermined distance. Examples of local area communication techniques according to an embodiment may include, but are not limited to, wireless LAN, Wi-Fi, BLUETOOTH, ZIGBEE, Wi-Fi Direct (WFD), ultra wideband (UWB), infrared data association (IrDA), Bluetooth low energy (BLE), and near field communication (NFC).

The wired communication module 32 refers to a module for communication using electric signals or optical signals. Examples of wired communication techniques according to an embodiment may include communication via a twisted pair cable, a coaxial cable, an optical fiber cable, and an Ethernet cable.

The mobile communication module 33 transmits or receives wireless signals to or from at least one selected from a base station, an external terminal, and a server on a mobile communication network. The wireless signals may be voice call signals, video call signals, or various types of data for transmission and reception of text/multimedia messages.

The memory 40 stores various data processed by the ultrasound diagnosis apparatus 100. For example, the memory 40 may store medical data related to diagnosis of an object, such as ultrasound data and an ultrasound image that are input or output, and may also store algorithms or programs which are to be executed in the ultrasound diagnosis apparatus 100.

The memory 40 may be any of various storage media, e.g., a flash memory, a hard disk drive, EEPROM, etc. Furthermore, the ultrasound diagnosis apparatus 100 may utilize web storage or a cloud server that performs the storage function of the memory 40 online.

The input device 50 refers to a means via which a user inputs data for controlling the ultrasound diagnosis apparatus 100. The input device 50 may include hardware components, such as a keypad, a mouse, a touch panel, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 60 may control all operations of the ultrasound diagnosis apparatus 100. In other words, the controller 60 may control operations among the probe 2, the ultrasound transceiver 10, the image processor 20, the communication module 30, the memory 40, and the input device 50 shown in FIG. 1.

All or some of the probe 2, the ultrasound transceiver 10, the image processor 20, the communication module 30, the memory 40, the input device 50, and the controller 60 may be implemented as software modules. However, embodiments of the present invention are not limited thereto, and some of the components stated above may be implemented as hardware modules. Furthermore, at least one selected from the ultrasound transceiver 10, the image processor 20, and the communication module 30 may be included in the controller 60. However, embodiments of the present invention are not limited thereto.

FIG. 2 is a block diagram showing a configuration of a wireless probe according to an embodiment.

As described above with reference to FIG. 1, the wireless probe 200 may include a plurality of transducers, and, according to embodiments, may include some or all of the components of the ultrasound transceiver 10 shown in FIG. 1.

The wireless probe 200 according to the embodiment shown in FIG. 2 includes a transmitter 210, a transducer 220, and a receiver 230. Since descriptions thereof are given above with reference to FIG. 1, detailed descriptions thereof will be omitted here. In addition, according to embodiments, the wireless probe 200 may selectively include a reception delaying unit 233 and a summing unit 234.

The wireless probe 200 may transmit ultrasound signals to the object 1, receive echo signals from the object 10, generate ultrasound data, and wirelessly transmit the ultrasound data to the ultrasound diagnosis apparatus 100 shown in FIG. 1.

Since ultrasound diagnosis apparatuses are large and expensive equipment, general users other than skilled persons working for professional organizations have difficulty in utilizing the ultrasound diagnosis apparatuses. However, ultrasound diagnosis apparatuses have currently become miniaturized with developments in technology, and the prices of ultrasound diagnosis apparatuses have reached low enough levels for general users to purchase the ultrasound diagnosis apparatuses. When a general user utilizes an ultrasound diagnosis apparatus, he or she can obtain an ultrasound image at home. Thus, even general users can simply observe the inside of their bodies and can be diagnosed remotely by providing acquired ultrasound images to a remote skilled user.

However, since it is difficult to manipulate ultrasound diagnosis apparatuses, if a user has no background knowledge, it is difficult to position a probe at a body part that is to be measured, and it is also difficult to set suitable image modes according to body parts.

An ultrasound imaging apparatus according to an exemplary embodiment of the present disclosure enables even users unskilled at manipulating ultrasound imaging apparatuses to easily acquire an ultrasound image. An ultrasound diagnosis apparatus and method and a computer-readable storage medium having the ultrasound diagnosis method recorded thereon, according to an exemplary embodiment of the present disclosure, will now be described in detail with reference to FIGS. 3-22.

The ultrasound diagnosis apparatus may construct an ultrasound image by acquiring a signal from a probe, and then may measure a length, an angle, an area, a volume, and the like of a particular organ, a particular structure, and the like on the ultrasound image. Via this measurement, the ultrasound diagnosis apparatus may acquire information about an abnormal part within a body or acquire information about a gestational age or the like. The ultrasound diagnosis apparatus is frequently used in a medical field because the ultrasound diagnosis apparatus is important means for assisting a medical diagnosis. Thus, if an inspection target is able to acquire an ultrasound image at home and transmit the ultrasound image to a remote medical expert, the inspection target can be diagnosed by the medical expert without visiting a hospital. For example, if an inspection target is able to acquire an ultrasound image at home and transmit the ultrasound image to a remote medical expert, the inspection target may acquire an ultrasound image at home immediately when he or she feels wrong with his or her body, and transmit the ultrasound image to a medical expert. Moreover, since the inspection target is able to acquire an ultrasound image at any time without restrictions on the time and the space, the inspection target is able to more minutely observe, for example, the progress of a body disease of the inspection target or the development process of a fetus.

FIG. 3 schematically illustrates use of an ultrasound diagnosis apparatus according to an exemplary embodiment of the present disclosure. Since a probe 310 of FIG. 3 corresponds to the probe 2 of FIG. 1 or the probe 200 of FIG. 2, a repeated description thereof will be omitted here.

According to an exemplary embodiment of the present disclosure, a user 260 may acquire an ultrasound image by using the probe 310. The probe 310 may be connected to a desktop 305 via wires or wirelessly.

FIG. 3 illustrates a case where the user 260 is identical to an inspection target. However, exemplary embodiments of the present disclosure are not limited thereto, and the user 260 may be a person who uses the ultrasound diagnosis apparatus to diagnose an inspection target.

The user 260 may position the probe 310 at a body part of which an ultrasound image is desired to be acquired. The desktop 305 may acquire an ultrasound image, based on ultrasound data received from the probe 310. The acquired ultrasound image may be displayed on a display unit included in the desktop 305.

Since ultrasound waves are unable to pass through the air within bones or a stomach, the diagnosis accuracy of an acquired ultrasound image may vary according to a location of a probe. Thus, a user who is unskilled at using ultrasound diagnosis apparatuses has difficulty in ascertaining a suitable location at which a probe is to be positioned in order to obtain an ultrasound image of a desired internal part of a body. The ultrasound diagnosis apparatus according to an exemplary embodiment of the present disclosure enables even an unskilled user to easily acquire an ultrasound image, by providing a "reference location" of a probe, which is suitable to obtain the ultrasound image.

The reference location denotes a location of a probe that is determined to be suitable to acquire an ultrasound image of a predetermined body part. The predetermined body part denotes a part of an inspection target, of which an ultrasound image may be acquired, such as a liver, a kidney, or a heart. For example, when a user desires to acquire an ultrasound image of a liver, the reference location may be the abdominal walls below the bone above the pit of the stomach and the right ribs.

The desktop 305 may acquire a relative location of the probe 310 with respect to the user 260, based on the acquired ultrasound image. The desktop 305 may include a photographing unit 271, and the photographing unit 271 may photograph the user 260 and the probe 310. The desktop 305 may acquire a relative location of the probe 310 with respect to the user 260, based on an image captured by the photographing unit 271.

The desktop 305 may display, to the user 260, a screen image including the location of the probe 310, the reference location, and a path from the location of the probe 310 to the reference location. The user 260 may position the probe 310 at the reference location along the path displayed on the display unit of the desktop 305. When the location of the probe 310 corresponds to the reference location, the desktop 305 may perform a predetermined operation. For example, the desktop 305 may inform the user 260 that the location of the probe 310 corresponds to the reference location, according to a predetermined method. The desktop 305 may also acquire an ultrasound image from the reference location. The desktop 305 may transmit the acquired ultrasound image to a remote medical expert. The remote medical expert may diagnose the inspection target, based on the received ultrasound image.

FIG. 4 is a block diagram of an ultrasound diagnosis apparatus 300 according to an exemplary embodiment of the present disclosure.

Referring to FIG. 4, the ultrasound diagnosis apparatus 300 includes a probe 310 and a desktop 305. The desktop 305 includes a control unit 320, a probe location acquisition unit 330, a display unit 340, and an image generation unit 350. The probe 310, the control unit 320, the display unit 340, and the image generation unit 350 of FIG. 4 may respectively correspond to the probe 2, the control unit 60, the display unit 25, and the image generation unit 24 of FIG. 1. Alternatively, the probe 310 may correspond to the probe 200 of FIG. 2.

The probe 310 may be connected to the desktop 305 via wires or wirelessly. The probe 310 may transmit an ultrasound signal to a target according to a control signal transmitted by the desktop 305, and receive a response signal (or an ultrasound echo signal) reflected by the object to form a reception signal. The probe 310 may form ultrasound image data by focusing the reception signal, and may transmit the ultrasound image data to the desktop 305. The image generation unit 350 included in the desktop 305 may generate an ultrasound image by using the ultrasound image data received from the probe 310. The display unit 340 may display the generated ultrasound image.

The desktop 305 may not only be a general cart-type or portable ultrasound apparatus but also be a general computer including a processor, such as a tablet, a personal computer (PC), or a laptop. The desktop 305 may be connected to the probe 310 via wires or wirelessly. The desktop 305 may receive information from the probe 310 and perform various operations to acquire an ultrasound image.

The probe 310 acquires ultrasound data regarding the object. The image generation unit 350 generates an ultrasound image of the object by using the ultrasound data. The probe location acquisition unit 330 acquires a location of the probe 310 on the object. The display unit 340 displays the location of the probe 310 and a predetermined reference location on an image representing the object. The control unit 320 determines whether the location of the probe 310 corresponds to the reference location.

The image representing the object is an image that is displayed on the display unit 340, and may be an actual image obtained by photographing an inspection target. The image representing the object may be a figure that represents the body of the inspection target. Portions of the image representing the object may respectively correspond to body parts of the inspection target.

When it is determined that the location of the probe 310 does not correspond to the reference location, the control unit 320 may determine a movement path to be taken by the probe 310 to move to the reference location. The display unit 340 may also display the movement path from the location of the probe 310 to the reference location on the image representing the object. When it is determined that the location of the probe 310 corresponds to the reference location, the control unit 320 may control the display unit 340 to display an image representing that the location of the probe 310 corresponds to the reference location. When the location of the probe 310 corresponds to the reference location, the control unit 320 may also control the probe 310 to transmit the ultrasound signal to the object and receive an echo signal from the object to acquire the ultrasound data.

The probe location acquisition unit 330 may acquire a location of the probe 310 with respect to the object. The probe location acquisition 330 may acquire a spatial distance and a spatial direction from a predetermined reference point of the object to the probe 310 as the location of the probe 310, or divide the object into a plurality of areas and acquire as the location of the probe 310 an area that is closest to the probe 310 or an area that the probe 310 contacts. The location of the probe 310 may be displayed on the image representing the object.

Alternatively, the probe location acquisition unit 330 may include a location tracking sensor that is included in the probe 310 or attached to the probe 310.

For example, the probe location acquisition unit 330 may be located outside the probe 310. The probe location acquisition unit 330 may acquire the location of the probe 310 by tracking a movement of the probe 310 on the basis of a predetermined point within a space where the ultrasound diagnosis apparatus 300 is located. A method of tracking a movement of the probe 310 by using a location tracking sensor is well known, and thus a detailed description thereof will be omitted here.

For example, the ultrasound diagnosis apparatus 300 may further include an input unit for receiving a user input of selecting at least one location from a plurality of locations on the object, and the control unit 320 may determine the selected location as the reference location. The ultrasound diagnosis apparatus 300 may further include a communication unit for receiving, from an external device, information used to determine the reference location, and the control unit 320 may determine the reference location based on the received information.

The ultrasound diagnosis apparatus 300 may display the reference location on the display unit 340. A user may easily position the probe 310 at the reference location, based on the location of the probe 310 and the reference location displayed on the display unit 340.

FIG. 5 is a block diagram of an ultrasound diagnosis apparatus 300 according to an exemplary embodiment of the present disclosure.

Referring to FIG. 5, the ultrasound diagnosis apparatus 300 may further include a photographing unit 460, a communication unit 470, a storage unit 480, and an input unit 490, in addition to the components of the ultrasound diagnosis apparatus 300 of FIG. 4.

The photographing unit 460 may photograph the probe 310 and the object. The probe location acquisition unit 330 may detect an area corresponding to the probe 310 and an area corresponding to the object from an image obtained by photographing the probe 310 and the object, and acquire the location of the probe 310 based on a location of the area corresponding to the probe 310 with respect to the area corresponding to the object.

The photographing unit 460 is an image capturing apparatus, and a camcorder, a webcam, a digital camera, or the like may be used as the photographing unit 460. A recent camera that is used in game players and PCs and is capable of motion recognition may be used as the photographing unit 460. The ultrasound diagnosis apparatus 300 may further include the photographing unit 460 photographing the probe 310 and the object, and the probe location acquisition unit 330 may detect an area corresponding to the probe 310 and an area corresponding to the object from the image obtained by photographing the probe 310 and the object, and acquire the location of the probe 310 based on the location of the area corresponding to the probe with respect to the area corresponding to the object.

The communication unit 470 may correspond to the communication unit 30 of FIG. 1. When the location of the probe 310 corresponds to the reference location, the communication unit 470 may transmit an ultrasound image to an external device. The communication unit 470 may receive information used to determine the reference location, from the external device. The communication unit 470 may transmit at least one selected from the location of the probe 310, the reference location, the ultrasound image, and an image that is displayed on the display unit 340 to the external device. The communication unit 470 may receive, from the external device, information used to generate the ultrasound image, and the control unit 320 may control at least one selected from the probe 310 and the image generation unit 350, based on the received information.

The storage unit 480 may correspond to the memory 40 of FIG. 1. The storage unit 480 may map a plurality of locations of the probe 310 with a plurality of reference ultrasound images and store a result of the mapping. The probe location acquisition unit 330 may compare the ultrasound image with the plurality of reference ultrasound images, select one from among the plurality of reference ultrasound images based on a result of the comparison, and acquire a location corresponding to the selected reference ultrasound image as the location of the probe 310.

A detailed operation of the ultrasound diagnosis apparatus 300 will now be described in detail with reference to FIGS. 6A-22. FIGS. 6A and 6B explain a method in which the ultrasound diagnosis apparatus 300 operates, according to an exemplary embodiment of the present disclosure.

FIG. 6A illustrates acquisition of an ultrasound image by a user 510 using the probe 310, according to an exemplary embodiment of the present disclosure. Referring to FIG. 6A, the user 510 is identical to an inspection target, a body part of which an ultrasound image is to be acquired. However, exemplary embodiments of the present disclosure are not limited thereto, and the user 510 may be a person who uses the ultrasound diagnosis apparatus 300 to diagnose the inspection target, such as a friend or a family of the inspection target.

For convenience of explanation, a case where the user 510 is identical with the inspection target will now be illustrated. The user 510 may position the probe 310 at an arbitrary location 511 of the body of the user 510. The probe 310 may be positioned at a location corresponding to a body part of which an ultrasound image is desired to be acquired by the user 510, but may be positioned at a wrong location due to lack of background knowledge of the user 510. For example, even when the user 510 desires to acquire an ultrasound image of a liver, the user 510 may position the probe 310 at a location inappropriate for acquiring an image of the liver, due to being unaware of the location of the liver within his or her body.

FIG. 6B illustrates a desktop 305 according to an exemplary embodiment of the present disclosure.

Referring to FIG. 6B, the image generation unit 350 may generate an ultrasound image 534, based on the ultrasound data acquired by the probe 310. The ultrasound image 534 may be displayed on the display unit 340. The storage unit 480 may map the plurality of locations of the probe 310 with the plurality of reference ultrasound images and store a result of the mapping. The plurality of reference ultrasound images may include ultrasound images serving as respective standards of body parts of the body of the user 510. The probe location acquisition unit 330 may compare the ultrasound image 534 generated by the image generation unit 350 with the plurality of reference ultrasound images. The probe location acquisition unit 330 may select a reference ultrasound image corresponding to the ultrasound image 534 from among the plurality of reference ultrasound images, according to a result of the comparison. For example, the probe location acquisition unit 330 may select a reference ultrasound image that is the most similar to the ultrasound image 534. For example, the probe location acquisition unit 330 may calculate a correlation between the ultrasound image 534 and each of the reference ultrasound images, which are stored in the storage unit 480. The probe location acquisition unit 330 may select a reference ultrasound image having the highest correlation with the ultrasound image 534.

The probe location acquisition unit 330 may determine a body part corresponding to the selected reference ultrasound image as a location 531 of the probe 310. The location 531 of the probe 310 may be acquired in real time as the user 510 moves the probe 310. The location 531 of the probe 310 may be displayed together with an image 535 representing the object, on the display unit 340.

Based on the body part of which the user 510 desires to acquire an ultrasound image, the ultrasound diagnosis apparatus 300 may determine a reference location of the probe 310 which is used to acquire the ultrasound image of the body part. The ultrasound diagnosis apparatus 300 may display a reference location 533 together with the image 535 representing the object, on the display unit 340. The ultrasound diagnosis apparatus 300 may display a path 532 from the location 531 of the probe 310 to the reference location 533, on the image 535 representing the object.

Thus, the user 510 may move the probe 310 while checking in real time the location 531 of the probe 310 and the reference location 533 displayed on the display unit 340. The user 510 may move the probe 310 while checking in real time the path 532 from the location 531 of the probe 310 to the reference location 533. The user 510 may move the probe 310 at the reference location 533, which is suitable for acquiring the ultrasound image, by moving the probe 310 along the path 532 provided by the ultrasound diagnosis apparatus 300.

For example, when the user 510 desires to acquire an ultrasound image of a liver, the ultrasound diagnosis apparatus 300 may determine, as the reference location, a location of the probe 310 that is suitable for acquiring the ultrasound image of the liver. The ultrasound diagnosis apparatus 300 may display the determined reference location on the image 535 representing the object. Thus, the user 510 of the ultrasound diagnosis apparatus 300 may easily move the probe 310 to the reference location, even when the user 510 has no background knowledge about the reference location of the probe 310 that is suitable for acquiring the ultrasound image of the liver.

FIG. 7 explains a method in which the ultrasound diagnosis apparatus 300 operates, according to an exemplary embodiment of the present disclosure.

The desktop 305 may further include a photographing unit 640 photographing the probe 310 and the object, and the probe location acquisition unit 330 may detect an area corresponding to the probe 310 and an area corresponding to the object from an image obtained by photographing the probe 310 and the object, and acquire the location of the probe 310 based on a location of the area corresponding to the probe 310 with respect to the area corresponding to the object.

For example, referring to FIG. 7, a user 610 may position the probe 310 at an arbitrary part 611 of the body of the user 610, similar to FIG. 6A. The photographing unit 640 may photograph the user 610 and the probe 310. Although the photographing unit 640 photographs the entire body in FIG. 7, exemplary embodiments of the present disclosure are not limited thereto. The photographing unit 640 may photograph a portion of the body of the inspection target. The probe location acquisition unit 330 may acquire a location 631 of the probe 310, based on an image captured by photographing the user 610 and the probe 310.

The probe location acquisition unit 330 may acquire an area corresponding to the probe 310 from the captured image. The probe location acquisition unit 330 may acquire the location 631 of the probe 310 on an image 635 representing the object, based on a location of the area corresponding to the probe 310 on an image 635 representing the object. The location 631 of the probe 310 may be acquired in real time as the user 610 moves the probe 310. A sensor may be attached to the probe 310 and acquire the location 631 of the probe 310. The location 631 of the probe 310 may be displayed together with the image 635 representing the object, on the display unit 340.

The display unit 340 may display an ultrasound image 634 generated by the image generation unit 350. A predetermined reference location 633 may be displayed together with the image 635 representing the object, on the display unit 340. A path 632 from the location 631 of the probe 310 to the reference location 633 may be displayed together with the image 635 representing the object, on the display unit 340.

FIGS. 8A and 8B illustrate screen images of an ultrasound diagnosis apparatus according to an exemplary embodiment of the present disclosure.

Referring to FIG. 8A, a display unit 760 may display an ultrasound image 764 generated by the image generation unit 350, and an image 766 representing the object. When a location 761 of the probe 310 and a predetermined reference location 763 are acquired, the display unit 760 may display the location 761 of the probe 310 and the predetermined reference location 763. The location 761 of the probe 310 may be updated in real time and displayed on the display unit 760, and a user may move the probe 310 while checking the updated location 761 of the probe 310. Thus, the user may easily move the location 761 of the probe to the predetermined reference location 763.

FIG. 8B illustrates a screen image according to another exemplary embodiment of the present disclosure. When it is determined that the location of the probe 310 does not correspond to a reference location, the control unit 320 may determine a movement path to be taken by the probe 310 to move to the reference location. The display unit 340 may display a movement path from the location of the probe 310 to the reference location on an image representing the object.

A display unit 710 may display an ultrasound image 714 generated by the image generation unit 350, and an image 716 representing the object. The ultrasound diagnosis apparatus 300 may acquire a location 711 of the probe 310 and a predetermined reference location 713. The display unit 710 may display the location 711 of the probe 310 and the predetermined reference location 713.

According to an exemplary embodiment of the present disclosure, when it is determined that the location 711 of the probe 310 does not correspond to the reference location 713, the control unit 320 may determine a path 712 to be taken to move the location 711 of the probe 310 to the reference location 713. For example, the path 712 may be a shortest distance from the location 711 of the probe 310 to the reference location 713. The path 712 may be a path for acquiring an optimal ultrasound image of the object.

The location 711 of the probe 310 may be changed in real time as the user moves the probe 310. The control unit 320 may determine the path 712 in real time, based on the changed location 711 of the probe 310. The path 712 may be displayed together with the image 716 representing the object, on the display unit 710. The user may easily move the location 711 of the probe 310 to the reference location 713 while checking the location 711 of the probe 310, the path 712, and the reference location 713, which are displayed on the display unit 710.

According to an exemplary embodiment of the present disclosure, the communication unit 470 may receive information related to the reference location 713 and the path 712 from a remote user, and the control unit 320 may acquire the reference location 713 and the path 712 based on the received information.

FIGS. 9A-9C explain a method in which the ultrasound diagnosis apparatus 300 operates, according to an exemplary embodiment of the present disclosure.

When a location of the probe 310 corresponds to a reference location, the control unit 320 may control the display unit 340 to display an image representing that the location of the probe 310 corresponds to the reference location. When the location of the probe 310 corresponds to the reference location, the control unit 320 may also control the probe 310 to transmit an ultrasound signal to the object and receive an echo signal from the object to acquire ultrasound data.

For example, FIG. 9A illustrates a case where a user 810 is identical with an inspection target, but exemplary embodiments of the present disclosure are not limited thereto. The user 810 may be a person who uses the ultrasound diagnosis apparatus 300 to diagnose the inspection target. The user 810 may position the probe 310 at a reference location 813 by moving the probe 310 along a path 812 from an initial location 811. The control unit 320 may determine whether the reference location 813 corresponds to a location of the probe 310. When the location of the probe 310 corresponds to the reference location 813, the control unit 320 may control the display unit 340 to display an image representing that the location of the probe 310 corresponds to the reference location 813. Although not shown in the drawings, when the location of the probe 310 corresponds to the reference location 813, the control unit 320 may inform the user 810 that the location of the probe 310 corresponds to the reference location 813, via sound, light, vibration, or the like instead of via the image.

For example, FIG. 9B illustrates an image representing that the location of the probe 310 corresponds to a reference location, according to an exemplary embodiment of the present disclosure. A display unit 820 may display an image 821 representing a target, together with an ultrasound image 823. When the location of the probe 310 corresponds to the reference location, the control unit 320 may control an icon 822 representing the reference location to flicker. Alternatively, when the location of the probe 310 corresponds to the reference location, the control unit 320 may control the entire screen image to flicker. However, exemplary embodiments of the present disclosure are not limited thereto, and the ultrasound diagnosis apparatus 300 may inform a user that the probe 310 has reached a reference location suitable for acquiring an ultrasound image, by notifying the user that the reference location corresponds to the location of the probe 310, via sound, vibration, or the like.

For example, FIG. 9C illustrates an image that may be displayed when the location of the probe 310 corresponds to a reference location, according to an exemplary embodiment of the present disclosure. A display unit 830 may display an image 831 representing a target, together with an ultrasound image 832. When the location of the probe 310 corresponds to the reference location, the control unit 320 may control the location of the probe 310, a path, and the reference location to disappear. A user may easily determine whether the probe 310 has reached the reference location, by checking whether the location of the probe 310, the path, and the reference location have disappeared from the display unit 830.

When the location of the probe 310 corresponds to the reference location, the ultrasound diagnosis apparatus 300 may control the probe 310 to transmit an ultrasound signal to the object and receive an echo signal from the object to acquire ultrasound data. The image generation unit 350 may generate an ultrasound image, based on the acquired ultrasound data. The acquired ultrasound image 823 or 832 may be displayed on the display unit 820 or 830.

The ultrasound diagnosis apparatus 300 may determine whether the acquired ultrasound image 823 or 832 is abnormal, by comparing the acquired ultrasound image 823 or 832 with a predetermined ultrasound image. The ultrasound diagnosis apparatus 300 may suggest the inspection target to visit a professional medical organization to receive a diagnosis, according to a result of the determination. The ultrasound diagnosis apparatus 300 may also suggest the inspection target to acquire an ultrasound image of another body part that may be necessary for diagnosis in association with the acquired ultrasound image 823 or 832. The ultrasound diagnosis apparatus 300 may enable a medical diagnosis to be made with respect to the ultrasound image 823 or 832, by transmitting the ultrasound image 823 or 832 to the professional medical organization in response to a user input.

FIGS. 10A and 10B explain a method in which the ultrasound diagnosis apparatus 300 interoperates with an external device, according to an exemplary embodiment of the present disclosure.

FIGS. 10A and 10B illustrate cases where users 1100 and 1190 are identical with inspection targets, but exemplary embodiments of the present disclosure are not limited thereto. The user 1100 may be a person who uses the ultrasound diagnosis apparatus 300 to diagnose the inspection target.

When the user 1100 wants to receive a diagnosis from a remote medical expert 1144, the user 1100 may request the remote medical expert 1144 for the diagnosis. The remote medical expert 1144 may request the ultrasound diagnosis apparatus 300 to acquire an ultrasound image, via an external device 1145. The ultrasound diagnosis apparatus 300 may enable a remote medical examination to be performed by the remote medical expert 1144, by interoperating with the external device 1145 as described below.

As shown in FIG. 10A, in response to a request from the remote medical expert 1144 to acquire an ultrasound image, the user 1100 may position the probe 310 at an arbitrary body part 1102. The ultrasound diagnosis apparatus 300 may acquire a current location of the probe 310 and display the current location of the probe 310 on a display unit 1120. For example, as shown in FIG. 10A, the ultrasound diagnosis apparatus 300 may display a location 1122 of the probe 310 on an image 1121 representing a target. The communication unit 470 may transmit/receive information to/from the external device 1145, as indicated by reference numeral 1130. For example, the communication unit 470 may transmit the location 1122 of the probe 310 and an ultrasound image 1123 to the external device 1145.

A display unit 1140 of the external device 1145 may display the same screen image as that displayed on the display unit 1120 of the user 1100. For example, the display unit 1140 of the external device 1145 may display an ultrasound image 1143. An image 1141 representing the object, together with a location 1142 of the probe 310, may be displayed on the display unit 1140. The location 1142 of the probe 310 and the ultrasound image 1143, which are provided via the ultrasound diagnosis apparatus 300, may respectively correspond to the location 1122 of the probe 310 and the ultrasound image 1123, which are provided via the external device 1145. For example, the whole or a portion of a screen image that is provided to the user 1100 via the ultrasound diagnosis apparatus 300 may be provided to the remote medical expert 1144 via the external device 1145. In other words, the medical expert 1144 may receive the same screen image as that received by the user 1100.

Since the user 1100 positions the probe 310 at any location without special knowledge about a body part desired to be observed by the medical expert 1144, the location 1142 of the probe 310 positioned by the user 1100 may not be a location (that is, a reference location) suitable for acquiring an ultrasound image of the body part desired to be observed by the medical expert 1144. The medical expert 1144 may transmit information related to the reference location to the ultrasound diagnosis apparatus 300 via the external device 1145. The ultrasound diagnosis apparatus 300 may receive the information related to the reference location and display the reference location to the user 1100. The user 1100 may change the location of the probe 310, based on the displayed reference location.

Referring to FIG. 10B, a remote medical expert 1156 may determine information used to determine a reference location 1154, by checking an ultrasound image 1155 and a location 1152 of the probe 310 displayed on a display unit 1150. The information used to determine the reference location 1154 may be an accurate coordinate on the body, but may be a body part of which the medical expert 1156 desires to acquire an ultrasound image. An external device 1157 may receive the information used to determine the reference location 1154, from the medical expert 1156. The external device 1157 may also receive a path 1153 from the location 1152 of the probe 310 to the reference location 1154, from the medical expert 1156. For example, the medical expert 1156 may input the reference location 1154 and the path 1153 to an image 1151 representing a target, by using a mouse. The ultrasound diagnosis apparatus 300 may receive the information used to determine the reference location 1154 and the path 1153 from the external device 1157 via the communication unit 470. The ultrasound diagnosis apparatus 300 may acquire the reference location 1154, which is suitable for acquiring an ultrasound image, based on the received information used to determine the reference location 1154.

A display unit 1170 of the ultrasound diagnosis apparatus 300 may display a location 1172 of the probe 310, a path 1173, and a reference location 1174 on an image 1171 representing the object. A user 1190 may move the probe 310 from a location 1192 of the probe 310 to a reference location, based on the displayed path 1173 and the displayed reference location 1174.

When the probe 310 is positioned at a location suitable for scanning a body part of which an ultrasound image is desired to be acquired, the ultrasound diagnosis apparatus 300 may inform the user 1190 that the probe 310 is positioned at the suitable location, according to a predetermined method. The ultrasound diagnosis apparatus 300 may generate an ultrasound image of the body part of which an ultrasound image is desired to be acquired, and display the generated ultrasound image on the display unit 1170. The communication unit 470 may transmit the generated ultrasound image to the external device 1157. The generated ultrasound image may be displayed on the display 1150 of the external device 1157.

The medical expert 1156 may give a diagnosis, based on the ultrasound image displayed on the display unit 1150.

When the user 1190 is a user unskilled at manipulating the ultrasound diagnosis apparatus 300, the user 1190 may be unaccustomed to manipulating a function of the ultrasound diagnosis apparatus 300. In particular, the unskilled user 1190 has difficulty in transmitting an ultrasound signal from the probe 310 and adjusting, in a concrete way, a parameter that is used during processing a received echo signal (for example, a gain and a penetrating depth of the probe 310 and a frequency of the transmitted ultrasound signal).

Thus, the ultrasound diagnosis apparatus 300 may receive information that is used to generate an ultrasound image, from the external device 1157 via the communication unit 470. In this case, the external device 1157 may receive the information used to generate an ultrasound image, from the medical expert 1156. The ultrasound diagnosis apparatus 300 may control at least one selected from the probe 310 and the image generation unit 350, based on the received information.

For example the ultrasound diagnosis apparatus 300 may control a parameter including at least one selected from the gain, the penetrating depth, and the frequency of the probe 310, based on the received information. The controller 320 may also control a beamforming method such as timing adjustment of a beam, based on the received information. The ultrasound diagnosis apparatus 300 may also control image processing including at least one selected from noise removal, pixel interpolation, image continuation, and space composition to be performed, based on the received information.

According to an exemplary embodiment of the present disclosure, since the remote medical expert 1156 is able to manipulate the ultrasound diagnosis apparatus 300, the number of manipulations of the ultrasound diagnosis apparatus 300 by an unskilled user may be minimized. The medical expert 1156 may easily give a diagnosis, based on the ultrasound image controlled by the medical expert 1156.

FIG. 11 is a flowchart of a method of operating an ultrasound diagnosis apparatus 300, according to an exemplary embodiment of the present disclosure.

Referring to FIG. 11, in operation 1910, the ultrasound diagnosis apparatus 300 may acquire a location of a probe on a target. For example, the ultrasound diagnosis apparatus 300 may acquire the location of the probe on the object according to methods as described above with reference to FIGS. 5-7. For example the ultrasound diagnosis apparatus 300 may acquire the location of the probe by comparing an ultrasound image acquired at the location of the probe with a reference ultrasound image. The ultrasound diagnosis apparatus 300 may also acquire the location of the probe, based on an image captured by photographing the probe and the object. The ultrasound diagnosis apparatus 300 may also acquire the location of the probe by using a location tracking sensor. Detailed descriptions of the methods of acquiring the location of the probe have already been given above, and thus will be omitted here.

In operation 1920, the ultrasound diagnosis apparatus 300 may display the location of the probe and a predetermined reference location on an image representing the object. In operation 1930, the ultrasound diagnosis apparatus 300 may determine whether the location of the probe corresponds to the predetermined reference location. The reference location is a location that is adequate for the ultrasound diagnosis apparatus 300 to obtain an ultrasound image.

The ultrasound diagnosis apparatus operating method of FIG. 11 may be performed by the ultrasound diagnosis apparatus 300 of FIG. 5. Thus, a description of the method of FIG. 11 that has already been given above with reference to FIG. 5 will be omitted. The operation 1910 of acquiring the location of the probe may be performed by the probe location acquisition unit 330. The displaying operation 1920 may be performed by the display unit 340. The operation 1930 of determining whether the location of the probe corresponds to the predetermined reference location may be performed by the control unit 320.

When it is determined that the location of the probe corresponds to the reference location, the ultrasound diagnosis apparatus 300 may display an image representing that the location of the probe corresponds to the reference location. When it is determined that the location of the probe corresponds to the reference location, the ultrasound diagnosis apparatus 300 may transmit an ultrasound signal to the object and receive an echo signal from the object to thereby acquire ultrasound data. In other words, when the probe is positioned at a location that is the most adequate to acquire an ultrasound image, the ultrasound diagnosis apparatus 300 may automatically acquire the ultrasound data. Accordingly, the ultrasound diagnosis apparatus 300 may enable a user unskilled at manipulating the ultrasound diagnosis apparatus 300 to more conveniently acquire an accurate ultrasound image.

The ultrasound diagnosis apparatus 300 may determine whether an acquired ultrasound image is abnormal, by comparing the acquired ultrasound image with a predetermined ultrasound image. The ultrasound diagnosis apparatus 300 may suggest the inspection target to visit a professional medical organization to receive a diagnosis, according to a result of the determination. The ultrasound diagnosis apparatus 300 may also suggest the inspection target to acquire an ultrasound image of another body part that may be necessary for diagnosis in association with the acquired ultrasound image. The ultrasound diagnosis apparatus 300 may enable a medical diagnosis to be made with respect to the ultrasound image, by transmitting the ultrasound image to a professional medical organization in response to a user input.

FIG. 12 is a flowchart of a method of operating an ultrasound diagnosis apparatus 300 in order to determine a reference location, according to an exemplary embodiment of the present disclosure.

The reference location is a location of a probe that is suitable to acquire an ultrasound image of each body part. When a user selects a body part of which an ultrasound image is to be acquired, the ultrasound diagnosis apparatus 300 may acquire a reference location that is suitable to acquire the ultrasound image, based on the selected body part.

Referring to FIG. 12, in operation 2010, the ultrasound diagnosis apparatus 300 may display a menu for selecting a body part that is to be measured. The body part selection menu that is provided by the ultrasound diagnosis apparatus 300 will be described in detail later with reference to FIGS. 15-22.

In operation 2020, the ultrasound diagnosis apparatus 300 may receive a user input of selecting at least one body part from a plurality of body parts included in the body part selection menu. In operation 2030, the ultrasound diagnosis apparatus 300 may determine a reference location, based on the selected body part. For example, the storage unit 480 may store a reference location that is suitable to acquire an ultrasound image corresponding to each body part. The ultrasound diagnosis apparatus 300 may select a reference location corresponding to the selected body part from among the stored reference locations.

In operation 2040, the ultrasound diagnosis apparatus 300 may acquire a location of a probe on an object. The method described above with reference to FIGS. 6A-7 may be equally applied to a method in which the probe location acquisition unit 330 acquires the location of the probe.

For example, to acquire the location of the probe, the ultrasound diagnosis apparatus 300 may acquire an ultrasound image and compare the acquired ultrasound image with a plurality of pre-stored reference ultrasound images. The ultrasound diagnosis apparatus 300 may select one from among the plurality of reference ultrasound images based on a result of the comparison, and acquire a location corresponding to the selected reference ultrasound image as the location of the probe.

As another example, to acquire the location of the probe, the ultrasound diagnosis apparatus 300 may photograph the probe and the object and acquire the location of the probe from an image captured by photographing the probe and the object.

In operation 2050, the ultrasound diagnosis apparatus 300 may display the acquired location of the probe and the determined reference location on an image representing the object, via the display unit 340. The display unit 340 may also display a path between the probe location and the reference location, on the image representing the object.

In operation 2060, the ultrasound diagnosis apparatus 300 may determine whether the location of the probe corresponds to the reference location. When the probe location does not correspond to the reference location, the ultrasound diagnosis apparatus 300 may return to operation 2040 to acquire the location of the probe again.

When it is determined that the location of the probe does not correspond to the reference location, the ultrasound diagnosis apparatus 300 may determine a movement path to be taken by the probe 310 to move to the reference location. The ultrasound diagnosis apparatus 300 may display the movement path from the location of the probe to the reference location on the image representing the object. A user may move the probe to the reference location, based on the path from the location of the probe to the reference location which is provided by the ultrasound diagnosis apparatus 300.

When the probe location corresponds to the reference location, the ultrasound diagnosis apparatus 300 may perform a predetermined operation, in operation 2070. For example, when it is determined that the location of the probe corresponds to the reference location, the ultrasound diagnosis apparatus 300 may display an image representing that the location of the probe corresponds to the reference location.

When it is determined that the location of the probe corresponds to the reference location, the ultrasound diagnosis apparatus 300 may transmit an ultrasound signal to the object and receive an echo signal from the object to thereby acquire ultrasound data.

The ultrasound diagnosis apparatus 300 may determine whether an acquired ultrasound image is abnormal, by comparing the acquired ultrasound image with a predetermined ultrasound image. The ultrasound diagnosis apparatus 300 may suggest an inspection target to visit a professional medical organization to receive a diagnosis, according to a result of the determination. The ultrasound diagnosis apparatus 300 may also suggest the inspection target to acquire an ultrasound image of another body part that may be necessary for diagnosis in association with the acquired ultrasound image.

When it is determined that the location of the probe corresponds to the reference location, the ultrasound diagnosis apparatus 300 may transmit an ultrasound image of the object to an external device. For example, the ultrasound diagnosis apparatus 300 may provide an ultrasound image having high diagnosis accuracy to a remote medical expert, by transmitting an ultrasound image acquired via the probe 310 located at the reference location to an external device. The remote medical expert may perform a diagnosis, based on the received ultrasound image.

FIG. 13 is a process flow diagram of a method in which the ultrasound diagnosis apparatus 300 interoperates with an external device 2160, according to an exemplary embodiment of the present disclosure.

The ultrasound diagnosis apparatus 300 may enter a remote diagnosis mode, in operation 2110. In the remote diagnosis mode, a remote medical expert may diagnose an inspection target, based on an ultrasound image acquired in the house of the inspection target. In the remote diagnosis mode, since wire-wireless bidirectional communication is used, the remote medical expert and the inspection target may interoperate with each other. Since the remote medical expert is able to set various parameters of an ultrasound diagnosis apparatus, efficiency of medical treatment may improve.

When entering the remote diagnosis mode, the external device 2160 which is used by the remote medical expert and the ultrasound diagnosis apparatus 300 are connected to each other via wire-wireless bidirectional communication. For example, the ultrasound diagnosis apparatus 300 may enter a remote diagnosis mode, based on an input of a user who wants to be remotely diagnosed. As another example, the ultrasound diagnosis apparatus 300 may receive a request signal for entering a remote diagnosis mode from the external device 2160, and enter the remote diagnosis mode by transmitting a response signal to the request of the external device 2160.

The ultrasound diagnosis apparatus 300 may transmit at least one selected from a location of a probe, a reference location, an ultrasound image, and an image displayed on the display unit of the ultrasound diagnosis apparatus 300 to the external device 2160, in operation 2120. The external device 2160 may display the at least one selected from the location of the probe, the reference location, the ultrasound image, and the image displayed on the display unit, to the medical expert who uses the external device 2160. The medical expert may newly determine a body part of which an ultrasound image is desired to be acquired, based on information that is provided via the external device 2160. The medical expert may correct the reference location received by the external device 2160. The medical expert may input information used to determine the reference location, to the external device 2160. The information used to determine the reference location may be an accurate coordinate value on an image representing an object. Alternatively, the information used to determine the reference location may be the name of the body part of which an ultrasound image is desired to be acquired by the medical expert.

The ultrasound diagnosis apparatus 300 may receive the information used to determine the reference location from the external device 2160, in operation 2130. The ultrasound diagnosis apparatus 300 may acquire the reference location, based on the information used to determine the reference location. The ultrasound diagnosis apparatus 300 may determine whether the location of the probe corresponds to the reference location. When the probe location corresponds to the reference location, the ultrasound diagnosis apparatus 300 may perform a predetermined operation, in operation 2140. For example, the ultrasound diagnosis apparatus 300 may inform the user that the location of the probe corresponds to the reference location, according to a predetermined method. The ultrasound diagnosis apparatus 300 may also acquire an ultrasound image from the reference location. The ultrasound diagnosis apparatus 300 may transmit the acquired ultrasound image to a remote user. The ultrasound diagnosis apparatus 300 may transmit at least one selected from the ultrasound image acquired at the reference location and the image displayed on the display unit to the external device 2160, in operation 2150. The image displayed on the display unit may include a menu display region and measurement values acquired by the ultrasound diagnosis apparatus 300. The medical expert may diagnose the inspection target, based on the information received by the external device 2160.

FIG. 14 is a process flow diagram of a method in which the ultrasound diagnosis apparatus 300 interoperates with the external device 2160, according to an exemplary embodiment of the present disclosure. FIG. 14 is a more detailed process flow diagram of FIG. 13, and thus repeated descriptions thereof will be omitted here.

The external device 2160 may request the ultrasound diagnosis apparatus 300 to enter a remote diagnosis mode, in operation 2210. For example, when a user of the ultrasound diagnosis apparatus 300 wants to be diagnosed by a remote medical expert, the user may request the remote medical expert for a remote medical examination. The remote medical expert may determine that an ultrasound image is necessary for a diagnosis. In this case, the remote medical expert may request the ultrasound diagnosis apparatus 300 to acquire an ultrasound image, via the external device 2160.

The ultrasound diagnosis apparatus 300 may enter a remote diagnosis mode, based on a request of the external device 2160, in operation 2220. The ultrasound diagnosis apparatus 300 may transmit at least one selected from the location of the probe, the reference location, the ultrasound image, and the image displayed on the display unit to the external device 2160, in operation 2230. The ultrasound diagnosis apparatus 300 may receive the information used to determine the reference location from the external device 2160, in operation 2240. When the probe location corresponds to the reference location, the ultrasound diagnosis apparatus 300 may perform a predetermined operation, in operation 2250. The ultrasound diagnosis apparatus 300 may transmit at least one selected from an ultrasound image obtained at the reference location and the image displayed on the display unit to the external device 2160, in operation 2260. The ultrasound diagnosis apparatus 300 may receive information used to generate an ultrasound image from the external device 2160, in operation 2270. The control unit 320 may control at least one selected from the probe 310 and the image generation unit 350, based on the received information. The ultrasound diagnosis apparatus 300 may control at least one selected from the probe 310 and the image generation unit 350, based on the received information, in operation 2280.

For example, the control unit 320 may control a parameter including at least one selected from a gain, a penetrating depth, and a frequency of the probe 310, based on the received information. The control unit 320 may control a beamforming method such as timing adjustment of a beam, based on the received information. The control unit 320 may control image processing including at least one selected from noise removal, pixel interpolation, image continuation, and space composition to be performed, based on the received information.

FIGS. 15-22 explain a menu selecting method according to an exemplary embodiment of the present disclosure.

According to an exemplary embodiment of the present disclosure, a user may need to select a plurality of menus to use an ultrasound diagnosis apparatus. For example, the user may select a plurality of menus in hierarchical orders illustrated in FIGS. 15 and 19.

The user may be skilled or unskilled at using ultrasound diagnosis apparatuses.

According to an exemplary embodiment of the present disclosure, the user may select a mode of a menu that is provided by the ultrasound diagnosis apparatus, according to his or her skill. For example, the menus displayed in FIGS. 16-18 may be provided by the ultrasound diagnosis apparatus when the user is a skilled user. The menus displayed in FIGS. 20-22 may be provided by the ultrasound diagnosis apparatus when the user is an unskilled user.

FIG. 15 explains a menu that may be provided when a user skilled at using ultrasound diagnosis apparatuses uses an ultrasound diagnosis apparatus.

A selection menu on a general ultrasound diagnosis apparatus may be provided according to a hierarchical structure as illustrated in a block 910 of FIG. 15. In other words, a user may select one item from a block 911, select one item from a block 912, and then select one item from a block 913. For example, when the user wants to obtain an ultrasound image of a liver, the user may select a menu in an order of a B mode, an abdomen, and a liver. When the user wants to obtain an image of a flow of the blood within a heart, the user may sequentially select a Doppler mode, a color, and a heart.

For example, referring to FIG. 15, when using the ultrasound diagnosis apparatus 300, the user may select an image mode of the ultrasound diagnosis apparatus 300 and a body part of which an image is to be acquired. The block 910 indicates a hierarchical structure. The user may select from an uppermost menu to a lowermost menu. The block 911 may be a list representing an uppermost menu. The block 911, which is a list of an uppermost menu, may include at least one item from among a B-mode and a Doppler mode.

The block 912 may represent a list of a lower menu of the block 911. The block 912 may include at least one item from among a muscle skeleton, abdomen, a color, and a PW. The color denotes a color Doppler image, and the PW denotes a spectral Doppler image. A lower list of the B-mode item of the block 911 may include at least one item from among the muscle skeleton and the abdomen included in the block 912. A lower list of the Doppler mode item of the block 911 may include at least one from among the color and the PW included in the block 912.

The block 913 may represent a list of a lower menu of the block 912. The block 913 may include at least one item from among an arm, a leg, a liver, and a kidney. A lower list of the muscle skeleton item of the block 912 may include at least one item from among the arm and the leg included in the block 913. It may be easy for a skilled user having background knowledge about ultrasound diagnosis apparatuses to select a hierarchical menu in the order of the block 911, the block 912, and the block 913. Thus, the ultrasound diagnosis apparatus 300 may provide a menu for selecting a hierarchical menu in the order of the block 911, the block 912, and the block 913, to a skilled user.

FIGS. 16-18 explain menus that may be provided when a user skilled at using ultrasound diagnosis apparatuses uses an ultrasound diagnosis apparatus.

FIG. 16 illustrates a display unit 920 displaying a menu selection screen image, according to an exemplary embodiment of the present invention. The display unit 920 may include an ultrasound image display region 921 and a menu display region 922.

The menu display region 922 may display a list corresponding to the block 911. For example, the menu display region 922 may include a first list 923, which is a list of image modes. The first list 923 may include at least one item from among a B-mode and a Doppler mode. For example, a user 924 may select a B mode item 925 from the first list 923.

FIG. 17 is a subsequent view of FIG. 16, and illustrates a screen image displayed on a display unit 940 after the user 924 selects the B mode item 925. A menu display region 942 may display a list of the block 912, which is a lower list of the block 911. For example, the menu display region 942 may include a second list 943. The second list 943 may include at least one item from among the muscle skeleton and the abdomen which are included in a body part list. For example, a user 944 may select an abdomen item 945 from the second list 943.

FIG. 18 is a subsequent view of FIG. 17, and illustrates a screen image displayed on a display unit 960 after the user 944 selects the abdomen item 945. A menu display region 962 may display a list of the block 913, which is a lower list of the block 912. The menu display region 962 may display a list of detailed body parts. The user 964 may select one from the items included in the detailed body part list. For example, the menu display region 962 may include a third list 963. The third list 963 may include at least one item from among the liver and the kidney which are included in the detailed body part list. For example, a user 964 may select a liver item 965 from the third list 963. The ultrasound diagnosis apparatus 300 may determine a reference location, based on a selection by the user 964. The ultrasound diagnosis apparatus 300 may display information including at least one selected from a location of a probe, a path, and the reference location. The user 964 may position the probe 310 at the reference location, based on the information displayed on the display unit 960.

Even when at least one is selected from the first through third lists by a user in FIGS. 15-18, the ultrasound diagnosis apparatus 300 may acquire an ultrasound image from a reference location. For example, since a skilled user is able to know a reference location enabling an optimal ultrasound image to be acquired for a body part of which an ultrasound image is to be acquired, the skilled user may not need a reference location that is provided by the ultrasound diagnosis apparatus 300. The skilled user may select a B mode from the first list 923 as in FIG. 16, but may select no items from the second list 943 and the third list 963. The skilled user may acquire an ultrasound image of the B mode by positioning a probe at the reference location on the body of an inspection target.

However, a user unskilled at using the ultrasound diagnosis apparatus 300 may not know a location of the probe that is suitable to acquire an ultrasound image, and a method of setting a function of the ultrasound diagnosis apparatus 300 that is suitable for a body part of which an ultrasound image is desired to be acquired. For example, the unskilled user may want to acquire an ultrasound image of a liver. In this case, when the first list 923 for selecting a B mode or a Doppler mode is first displayed to the unskilled user, the unskilled user may not know what to select from the first list 923 in order to perform ultrasound measurement on a liver. In addition, the unskilled user has difficulty in knowing at which location the probe is to be positioned in order to acquire an ultrasound image of the liver.

Thus, the ultrasound diagnosis apparatus 300 may enable a user to select, according to his or her skill, a mode of a menu that is provided by the ultrasound diagnosis apparatus 300.

FIG. 19 explains a menu that may be provided when a user unskilled at using ultrasound diagnosis apparatuses uses an ultrasound diagnosis apparatus.

FIGS. 20-22 explain menus that may be provided when a user unskilled at using ultrasound diagnosis apparatuses uses an ultrasound diagnosis apparatus. According to an exemplary embodiment of the present disclosure, the ultrasound diagnosis apparatus 300 may enable a user to first select a body part of which an ultrasound image is to be acquired.

The selection by the user may be based on a hierarchical menu that is provided by the ultrasound diagnosis apparatus 300. A block 1010 indicates a hierarchical structure. A user may select a lowermost menu from an uppermost menu. A block 1011 may be a list representing an uppermost menu. The block 1011, which is a list of an uppermost menu, may include at least one item from among an arm, a leg, a liver, a kidney, a heart, and a neck. The user may select a detailed body part of which an ultrasound image is to be acquired, from among the items listed in the block 1011, which is the uppermost menu list.

A block 1012 may represent a list of a lower menu of the block 1011. The block 1012 may include at least one item from among a muscle skeleton, abdomen, and a color. A lower list of the liver item of the block 1011 may include at least one item from among the abdomen and the color included in the block 1012. The color denotes a color Doppler image.

A block 1013 may represent a list of a lower menu of the block 1012. The block 1013 may include at least one item from among a B-mode and a Doppler mode. A lower list of the muscle skeleton item of the block 1012 may include a B-mode item included in the block 1013.

Users having no background knowledge about ultrasound diagnosis apparatuses have difficulty in knowing an image mode that is to be selected in order to an ultrasound image of a predetermined body part, and a location at which a probe is to be positioned. Thus, the ultrasound diagnosis apparatus 300 may provide a hierarchical menu in the order of the block 1011, the block 1012, and the block 1013 such that even unskilled users may easily set a function of the ultrasound diagnosis apparatus 300.

FIG. 20 illustrates a display unit 1020 displaying a menu selection screen image, according to an exemplary embodiment of the present invention. The display unit 1020 may include an ultrasound image display region 1021 and a menu display region 1022. The ultrasound diagnosis apparatus 300 may display a body part selection menu on the menu display region 1022. A user 1025 may select a predetermined body part from the body part selection menu in order to acquire an image of the predetermined body part. The ultrasound diagnosis apparatus 300 may select a reference location corresponding to the selected body part.

According to an exemplary embodiment of the present disclosure, the ultrasound diagnosis apparatus 300 may display the body part selection menu on the menu display region 1022, in the form of a list. For example, the menu display region 1022 may display a first list (not shown) corresponding to the block 1011. In other words, the first list is a list of detailed body parts and thus may include at least one item from among an arm, a leg, a liver, a kidney, and a heart. For example, the user 1025 may select a liver item (not shown) from the third list.

According to an exemplary embodiment of the present disclosure, as shown in FIG. 20, the ultrasound diagnosis apparatus 300 may not display the body part selection menu in the form of a list, but may display the body part selection menu on an image 1023 representing the object. A plurality of body parts may be displayed on the image 1023 representing the object. For example, a plurality of circular icons, such as a body part 1024, may be displayed. The plurality of body parts may be locations corresponding to the items of the block 1011, respectively. For example, the user 1025 may select the body part 1024 from among the plurality of body parts displayed on the image 1023 representing the object. The body part 1024 may be a liver. Although not shown in FIG. 20, when the user 1025 selects the body part 1024, the display 1020 may represent that the liver has been selected, via a text. By displaying body parts of which ultrasound images are to be acquired on the image 1023 representing the object as described above, users may more easily select a body part of which an ultrasound image is to be acquired. Moreover, users may easily recognize visually where to locate the probe 310.

The ultrasound diagnosis apparatus 300 may acquire a location of the probe 310. The ultrasound diagnosis apparatus 300 may determine whether the location of the probe 310 corresponds to the reference location 1024 selected by the user 1025. When it is determined that the location of the probe 310 does not correspond to the reference location 1024 selected by the user 1025, the ultrasound diagnosis apparatus 300 may display a path on the image 1023 representing the object.

FIG. 21 is a subsequent view of FIG. 20, and illustrates a screen image displayed on a display unit 1040 after the user 1025 selects the body part 1024. A menu display region 1042 may display a list of the block 1012, which is a lower list of the block 1011. For example, the menu display region 1042 may include a second list 1043. The second list 1043 may include at least one item from among an abdomen and a color. For example, a user 1044 may select an abdomen item 1045 from the second list 1043.

FIG. 22 is a subsequent view of FIG. 21, and illustrates a screen image displayed on a display unit 1060 after the user 1044 selects the abdomen item 1025. A menu display region 1062 may display a list of the block 1013, which is a lower list of the block 1012. For example, the menu display region 1062 may include a third list 1063. The third list 1063 may include a B-mode item. For example, a user 1064 may select a B mode item 1065 from the third list 1063. When the user 1064 selects the B-mode item 1065, an ultrasound image display region 1061 of the display 1060 may display an image corresponding to an ultrasound B mode.

When a user is unskilled at using the ultrasound diagnosis apparatus 300, although a body part selected from the menu display region 1022 of the ultrasound diagnosis apparatus 300 by the user is a liver, the user may actually position the probe 310 at a location that is not the location of a liver. In this case, an ultrasound image displayed on the ultrasound image display region 1061 is not an ultrasound image of the liver. Accordingly, as described above with reference to FIGS. 5-9C, when the location of the probe 310 is different from the reference location, the control unit 320 may guide the probe 310 to be positioned at the liver which is the reference location.

Even when at least one is selected from the first through third lists by the user, the control unit 320 may control an ultrasound image to be acquired from the reference location. For example, the user may select a liver from detailed body parts included in the first list, but may select no items from the second list 1043 and the third list 1063. The ultrasound diagnosis apparatus 300 may acquire a reference location, based on the selected body part. The ultrasound diagnosis apparatus 300 may automatically select an ultrasound image mode that is adequate to acquire an ultrasound image of the liver. For example, the ultrasound image mode may be a B mode.

The ultrasound diagnosis apparatus 300 may display the acquired reference location on the display unit 340. The user may position the probe 310 at the reference location while checking the display unit 340. The ultrasound diagnosis apparatus 300 may acquire an ultrasound image when the probe 310 is positioned at the reference location.

The ultrasound diagnosis apparatus 300 may set information that is used to generate an ultrasound image, according to a body part selected by the user as a body part of which an ultrasound image is to be acquired. For example the ultrasound diagnosis apparatus 300 may set a parameter including at least one selected from a gain, a penetrating depth, and a frequency of a predetermined probe, based on the body part of which an ultrasound image is to be acquired. The ultrasound diagnosis apparatus 300 may set a beam-forming method as a predetermined method, based on the body part of which an ultrasound image is to be acquired. The ultrasound diagnosis apparatus 300 may perform image processing including at least one selected from noise removal, pixel interpolation, image continuation, and space composition, based on the body part of which an ultrasound image is to be acquired.

According to the present disclosure, general users may easily manipulate ultrasound diagnosis apparatuses and easily ascertain a reference location from which an optimal ultrasound image of a predetermined body part may be acquired, thereby acquiring an ultrasound image. Thus, the ultrasound diagnosis apparatus may have increased accuracy and may more rapidly acquire an ultrasound image.

A method according to an exemplary embodiment of the present invention may be embodied as program commands executable by various computer means and may be recorded on a non-transitory computer-readable recording medium. The computer-readable recording medium may include program commands, data files, data structures, and the like separately or in combinations. The program commands to be recorded on the computer-readable recording medium may be specially designed and configured for exemplary embodiments of the present invention or may be well-known to and be usable by one of ordinary skill in the art of computer software. Examples of the non-transitory computer-readable recording medium include a magnetic medium such as a hard disk, a floppy disk, or a magnetic tape, an optical medium such as a compact disk-read-only memory (CD-ROM) or a digital versatile disk (DVD), a magneto-optical medium such as a floptical disk, and a hardware device specially configured to store and execute program commands such as a ROM, a random-access memory (RAM), or a flash memory. Examples of the program commands are advanced language codes that can be executed by a computer by using an interpreter or the like as well as machine language codes made by a compiler.

The exemplary embodiments should be considered in a descriptive sense only and not for purposes of limitation. Descriptions of features or aspects within each exemplary embodiment should typically be considered as available for other similar features or aspects in other exemplary embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. An ultrasound diagnosis apparatus comprising:
   a probe configured to acquire ultrasound data of an object;
   an image generator configured to generate an ultrasound image of the object by using the ultrasound data;
   a location tracking sensor configured to acquire a location of the probe on the object;
   a display configured to display the location of the probe and a reference location on an image representing the object;
   a communication module configured to communicate with an external device in a remote diagnosis mode; and
   a controller configured to:
   control the communication module to transmit, to the external device, first information associated with determining the reference location based on the remote diagnosis mode;
   receive, via the communication module and from the external device, second information associated with determining the reference location, based on controlling the communication module to transmit the first information;
   determine the reference location based on the second information; and
   determine whether the location of the probe corresponds to the reference location.

2. The ultrasound diagnosis apparatus of claim 1, further comprising a storage configured to map a plurality of locations of the probe with a plurality of reference ultrasound images and store a result of the mapping,
   wherein the location tracking sensor is further configured to compare the ultrasound image with the plurality of reference ultrasound images, select one from among the plurality of reference ultrasound images based on a result of the comparison, and acquire a location corresponding to the selected reference ultrasound image as the location of the probe.

3. The ultrasound diagnosis apparatus of claim 1, further comprising a photographer configured to photograph the probe and the object, wherein the location tracking sensor is further configured to detect an area corresponding to the probe and an area corresponding to the object from an image captured by photographing the probe and the object, and acquire the location of the probe based on a location of the area corresponding to the probe with respect to the area corresponding to the object.

4. The ultrasound diagnosis apparatus of claim 1, wherein when it is determined that the location of the probe does not correspond to the reference location, the controller is further configured to determine a movement path to be taken by the probe to move to the reference location, and the display is further configured to display the movement path from the location of the probe to the reference location on the image representing the object.

5. The ultrasound diagnosis apparatus of claim 1, wherein, when the location of the probe corresponds to the reference location, the controller is further configured to control the display to display an image representing that the location of the probe corresponds to the reference location.

6. The ultrasound diagnosis apparatus of claim 1, wherein, when the location of the probe corresponds to the reference location, the controller is further configured to control the probe to transmit an ultrasound signal to the object and receive an echo signal from the object to acquire the ultrasound data.

7. The ultrasound diagnosis apparatus of claim 1, wherein the communication module is further configured to transmit the ultrasound image to the external device when the location of the probe corresponds to the reference location.

8. The ultrasound diagnosis apparatus of claim 1, further comprising an input interface configured to receive a user input of selecting at least one location from among a plurality of locations on the object, wherein the controller is further configured to determine the selected location as the reference location.

9. The ultrasound diagnosis apparatus of claim 1, wherein the first information associated with determining the reference location includes at least one selected from the location of the probe, the reference location, the ultrasound image, and an image displayed on the display to the external device.

10. The ultrasound diagnosis apparatus of claim 9, wherein
    the communication module is further configured to receive information that is used to generate the ultrasound image, from the external device, and
    the controller is further configured to control at least one selected from the probe and the image generator, based on the received information.

11. A method of operating an ultrasound diagnosis apparatus including a probe acquiring ultrasound data of an object and an image generator generating an ultrasound image of the object by using the ultrasound data, the method comprising:
    acquiring a location of the probe on the object;
    displaying the location of the probe and a reference location on an image representing the object;
    transmitting, to an external device, first information associated with determining the reference location based on a remote diagnosis mode of the ultrasound diagnosis apparatus;
    receiving, from the external device, second information associated with determining the reference location based on transmitting the first information;
    determining the reference location based on the second information; and
    determining whether the location of the probe corresponds to the reference location.

12. The method of claim 11, further comprising mapping a plurality of locations of the probe with a plurality of reference ultrasound images and storing a result of the mapping,
    wherein the acquiring of the location of the probe comprises:
    comparing the ultrasound image with the plurality of reference ultrasound images;
    selecting one reference ultrasound image from the plurality of reference ultrasound images, based on a result of the comparing; and
    acquiring a location corresponding to the selected reference ultrasound image as the location of the probe.

13. The method of claim 11, wherein the determining whether the location of the probe corresponds to the reference location comprises:
- determining a movement path to be taken by the probe to move to the reference location when it is determined that the location of the probe does not correspond to the reference location; and
- displaying the movement path from the location of the probe to the reference location on the image representing the object.

14. A non-transitory computer-readable recording medium having recorded thereon a program for executing the method of claim 11.

15. The ultrasound diagnosis apparatus of claim 1, wherein the controller is further configured to:
- receive a user input associated with a request to enter the remote diagnosis mode; and
- control the communication module to communicate with the external device based on the user input.

16. The ultrasound diagnosis apparatus of claim 1, wherein the controller is further configured to:
- receive, via the communication module and from the external device, a request to enter the remote diagnosis mode; and
- control the communication module to communicate the external device based on the request.

17. The ultrasound diagnosis apparatus of claim 1, wherein the first information permits the external device to display via a display of the external device at least one of the location of the probe, the reference location, the ultrasound image, or the image representing the object to permit a remote user to view the first information via the display of the external device.

18. The ultrasound diagnosis apparatus of claim 1, wherein the second information includes information input to the external device via a remote user.

19. The ultrasound diagnosis apparatus of claim 1, wherein the second information includes at least one of an accurate coordinate value or a name of a body part.

20. The ultrasound diagnosis apparatus of claim 1, wherein the controller is further configured to:
- perform a predetermined operation based on the probe location corresponding to the reference location;
- control the communication module to transmit, to the external device, at least one of an ultrasound image obtained at the reference location and an image displayed on the display;
- receive, via the communication module and from the external device, information used to generate an ultrasound image; and
- control at least one of the probe and the image generator based on the received information used to generate the ultrasound image.

* * * * *